(12) United States Patent
Fang et al.

(10) Patent No.: US 8,574,570 B2
(45) Date of Patent: Nov. 5, 2013

(54) BI-STABLE QUANTUM WIRE ARRAY OF SELF-ASSEMBLED NANOMEDICINE AND THE PREPARATION METHOD THEREFOR

(75) Inventors: Yan Fang, Shanghai (CN); Rong Wu, Shanghai (CN)

(73) Assignee: Zhongshan Hospital, Fudan University, Shanghai (CN)

( * ) Notice: Subject to any disclaimer, the term of this patent is extended or adjusted under 35 U.S.C. 154(b) by 913 days.

(21) Appl. No.: 12/008,904

(22) Filed: Jan. 15, 2008

(65) Prior Publication Data

US 2008/0166333 A1 Jul. 10, 2008

Related U.S. Application Data

(63) Continuation-in-part of application No. PCT/CN2006/000107, filed on Jan. 23, 2006.

(30) Foreign Application Priority Data

Jul. 15, 2005 (CN) .......................... 2005 1 0027795

(51) Int. Cl.
*A61K 38/44* (2006.01)
*C12N 9/00* (2006.01)

(52) U.S. Cl.
USPC ........... 424/94.4; 435/183; 977/702; 977/721

(58) Field of Classification Search
USPC ................... 424/94.4; 435/183; 977/702, 721
See application file for complete search history.

(56) References Cited

U.S. PATENT DOCUMENTS

| 5,589,692 | A | 12/1996 | Reed |
| 6,060,327 | A | 5/2000 | Keen |
| 2006/0292081 | A1 | 12/2006 | Morton et al. |

FOREIGN PATENT DOCUMENTS

| CN | 1049115 | C | 2/2000 | |
| CN | 2004/00099386 | | 12/2004 | ............. A61K 38/44 |
| DE | 198 52 543 | A | 5/2005 | |
| JP | 2003-076036 | A | 3/2003 | |

OTHER PUBLICATIONS

Abstract for Fang et al. "Mode-actions of the Na(+)-Ca2+ exchanger: from genes to mechanisms to a new strategy in brain disorders." Biomed Pharmacother. vol. 52.4 (1998) p. 145-156.
International Search Report for PCT/CN2006/000107 dated May 18, 2006.
Co-Pending U.S. Appl. No. 11/886,490, filed Sep. 17, 2007.
Co-Pending U.S. Appl. No. 12/002,888, filed Dec. 19, 2007.
Substitute Specification and Preliminary Amendment filed with Co-Pending U.S. Appl. No. 11/813,265 on Jul. 2, 2007.
Fang et al. "The mechanisms of synergy of four drugs in protecting cortico-cerebral function from anoxic damage," Zhongguo Yingyong Shenglixue Zazhi, 12(3), 1996, p. 223-226. (Abstract provided).
Yu et al. "Self-Assembly Techniques for Fabrications of Nanocomposite Thin Films." Wuhan Ligong Daxue Xuebao • Xinxi Yu Guangligongcheng Ban, 24(4), 2002, p. 137-141. (Abstract provided).

*Primary Examiner* — Taeyoon Kim
(74) *Attorney, Agent, or Firm* — Hamre, Schumann, Mueller & Larson, P.C.

(57) ABSTRACT

A bi-stable quantum wire array of self-assembled nano-medicine and its process present in the invention. The bi-stable quantum wire array with quantum bit and kondo effect is prepared by self-assembling an oxygen radical antagonist of antioxidase, a β-receptor agonist, a P2 receptor agonist, a calcium antagonist of phenyl alkyl amines, and/or a nucleotide monomer of purines and its binary, ternary, quaternary or quinary compounds and using the interaction of inelastic electron tunneling. The invention not only benefits mechanisms-targeted multifunctional device discoveries, but also profits inventions of nanometer structures, novel materials, quantum calculation devices, biosensors and quantum bit magnetic random access memories (MRAM).

8 Claims, 14 Drawing Sheets
(14 of 14 Drawing Sheet(s) Filed in Color)

BI-STABLE QUANTUM WIRE ARRAY OF SELF-ASSEMBLED NANOMEDICINE AND THE PREPARATION METHOD THEREFOR

RELATED APPLICATIONS

This application is a continuing application of International Application No. PCT/CN06/000107, filed Jan. 23, 2006, which designated the United States and claims priority to Chinese Patent Application Number CN 200510027795.6, filed Jul. 15, 2005.

The invention is made under governmental grants of national science foundation of China (NSFC30470409) and Shanghai science and technology committee (STC03JC14020&0452nm085) that should be acknowledged.

TECHNICAL FIELD

This invention relates to preparation processes of enabling liquid pharmaceutical ingredients to be self-assembled into bi-stable vertical quantum wire arrays and potential uses in artificial polymer molecular quantum information material and clinical nano-diagnostic tools.

BACKGROUND

Vertical bi-stable quantum wires are the key component of developing high performance quantum calculation and ultra-fast or ultra-sensitive diagnostic implanted nano-devices and nano-biosensors, and become the hot point of bioelectronics, informatics and advanced functional material nanometer manufactures. A long-standing research interest is to develop biological molecules-based implanted medical devices with quantum bit memory and self-charged. It has been revealed that inelastic electron tunneling and intermolecular coordination along with hydrogen bonds enable single molecular level pharmaceutical verapamil, isoprenaline, superoxide dismutase and adenosine triphosphate to be self-assembled into bi-stable nanometer vertical quantum wire arrays that possess quantum bit operator permutations and kondo effects at room temperature as well as multiple utilities of charge transports and target recognitions.

SUMMARY

In one aspect of the invention, nanomedicine self-assembling into vertical bi-stable quantum wire arrays are selected from liquid ingredients consisting of the unitary, binary, ternary, and quaternary ingredients of a β-adrenergic agonist, a $P_2$-purinergic agonist, a phenylalkylamine calcium channel blocker, an antioxidase antioxidant and/or nucleic acids according to the $L_{16}(2)^{15}$ and the $L_9(3)^4$ orthogonal schemes. The bi-stable quantum wire arrays with quantum bits and kondo effects at room temperature are prepared from self-assembled nanomedicine ingredients at a low temperature of −4° C. and identified by an interaction of point contact image (PCI) scanning probe microscopy and mathematical analysis workstations through inelastic electron tunneling and intermolecular energy coordinates.

The self-assembled nanomedicine in said bi-stable quantum wire array of self-assembled nanomedicine contains liquid ingredients as follows. The liquid ingredient of a β-adrenergic agonist includes isoprenaline. The concentration of the isoprenaline is in a range of from about 210 zeptoMol to about 0.001 zeptoMol. The liquid ingredient of a $P_2$-purinergic agonist includes adenosine triphosphate. The concentration of adenosine triphosphate is in a range of from about 260 zeptoMol to about 1 zeptoMol. The liquid ingredient of a phenylalkyl-amine calcium channel blocker includes verapamil. The concentration of verapamil is in a range of from about 20 zeptoMol to about 0.001 zeptoMol. The liquid ingredient of an antioxidase antioxidant includes superoxide dismutase. The concentration of superoxide dismutase is in a range of from about 1 zeptoMol to about 0.001 zeptoMol. The liquid ingredient of a nucleic acid includes xanthine. The concentration of xanthine is in a range of from about 50 μM to about 5 mM.

The unitary bi-stable quantum wire array of self-assembled nanomedicine can be a xanthine-based unitary nanomedicine self-assembly system, wherein the xanthine-based unitary nanomedicine self-assembly system is respectively selected from four groups of the $L_{16}(2)^{15}$ orthogonal design protocol at molar mixture ratios of (verapamil:isoprenaline:superoxide dismutase: adenosine triphosphate) according to (i) 1:0:0:0; (ii) 0:1:0:0; (iii) 0:0:1:0; (iv) 0:0:0:1, and combinations thereof. The binary bi-stable quantum wire array of self-assembled nanomedicine can be a xanthine-based binary nanomedicine self-assembly system, wherein the xanthine-based binary nanomedicine self-assembly system is respectively selected from the six groups of the $L_{16}(2)^{15}$ orthogonal design protocol at molar mixture ratios of (verapamil:isoprenaline:superoxide dismutase:adenosine triphosphate) according to (i) 1:1:0:0; (ii) 1:0:1:0; (iii) 1:0:0:1; (iv) 0:1:1:0; (v) 0:1:0:1; (vi) 0:0:1:1, and combinations thereof. The ternary bi-stable quantum wire array of self-assembled nanomedicine is a xanthine-based ternary nanomedicine self-assembly system, wherein the xanthine-based ternary nanomedicine self-assembly system is respectively selected from four groups of the $L_{16}(2)^{15}$ orthogonal design protocol at molar mixture ratios of (verapamil:isoprenaline:superoxide dismutase:adenosine triphosphate) according to (i) 1:1:1:0; (ii) 1:0:1:1; (iii) 1:1:0:1; (iv) 0:1:1:1, and combinations thereof. The quaternary bi-stable quantum wire array of self-assembled nanomedicine is a xanthine-based quaternary nanomedicine self-assembly system, wherein the xanthine-based quaternary nanomedicine self-assembly system is respectively selected in nine groups of the $L_{16}(2)^{15}$ and $L_9(3)^4$ orthogonal design protocol at molar mixture ratio of (verapamil:isoprenaline:superoxide dismutase:adenosine triphosphate) according to (i) 1:1:1:1; (ii) 1:2:2:2; (iii) 1:3:3:3; (iv) 2:1:2:3; (v) 2:2:3:1; (vi) 2:3:1:2; (vii) 3:1:3:2; (viii) 3:2:1:3; (ix) 3:3:2:1, and combinations thereof, and wherein (i) in the $L_9(3)^4$ orthogonal design protocol is overlapped with the quaternary molar ratio group in the $L_{16}(2)^{15}$ orthogonal design protocol.

The bi-stable quantum wire arrays of self-assembled nanomedicine are prepared by xanthine-based unitary, binary, ternary, or quaternary nanomedicine self-assembly in a preparation process comprising the steps as follows: (a) preparing a pharmaceutical standard solution of verapamil hydrochloride, a pharmaceutical standard solution of isoprenaline hydrochloride, a physiological buffer solution of superoxide dismutase, and a physiological buffer solution of adenosine triphosphate, respectively; (b) respectively mixing the optimum molar ratio of the selected ingredient solutions as mentioned in [0006] in a physiological buffer solution and/or a pharmaceutical standard solution according to $L_{16}(2)^{15}$ and $L_9(3)^4$ orthogonal design protocols; (c) immersing the silicon substrate into the desired ingredient mixture solutions as mentioned in [0006] to form bi-stable quantum wire arrays on the substrate; and (d) cooling the above mixed ingredient liquids at −4° C. for 96 hours on the substrates to form size-controlled bi-stable quantum wire arrays with quantum bits (qubits) and kondo effects at room temperature, wherein 3 dimensional (3D) nanometer size-controlled topographic structures of bi-stable quantum wire arrays with room temperature qubits can be identified by a PCI scanning probe microscopy (conducting atomic force microscopy, C-AFM) images and C-AFM electronic feature measurements, namely, current vs. voltage (I-V) curves and its analysis to decipher kondo effects (a maximum differential conductance peak around zero bias potential) in the $1^{st}$ derivative of I-V curves, spin-up and spin-down qubits ($\pm\frac{1}{2}\pi N$ electron spins at the z-axis orientation) and spin echo phenomena (no angular momentum at all at the z-axis orientation) in the energy-frequency-phase and the energy-time-phase spectra through the $1^{st}$ derivatives and fast Fourier transformation of I-V curves.

In another aspect of the invention, the bi-stable quantum wire arrays with room temperature kondo effects and qubits are crystallized at nanometers from one or more ingredients selected from liquid pharmaceutical groups consisting of (a) a β-adrenergic receptor agonist; (b) a $P_2$-purinergic receptor agonist; (c) a phenylalkylamine calcium channel blocker; and (d) an antioxidase antioxidant.

The preparation process of self-assembled bi-stable quantum wire arrays includes the following features: (1) the optimum self-assembly process of a bi-stable quantum wire comprises a crystallized process of liquid pharmaceutical ingredients on a substrate; (2) the optimum self-assembly process of the unitary bi-stable quantum wires comprises a selection process of liquid unitary pharmaceutical ingredients in either a β-adrenergic receptor agonist that includes isoprenaline, a $P_2$-purinergic receptor agonist that includes adenosine triphosphate, a phenylalkylamine calcium channel blocker that includes verapamil or an antioxidase antioxidant that includes superoxide dismutase, and/or a nucleic acid that includes xanthine; (3) the optimum self-assembly process of bi-stable quantum wires of unitary, binary, ternary, and quaternary nanomedicine comprises a crystallized process of xanthine-based unitary, binary, ternary, and quaternary pharmaceutical liquid ingredients on the substrates.

The unitary bi-stable quantum wire array is respectively crystallized from xanthine-based liquid ingredients at molar mixture ratios of (verapamil:isoprenaline: superoxide dismutase:adenosine triphosphate) according to (i) 1:0:0:0; (ii) 0:1:0:0; (iii) 0:0:1:0; and (iv) 0:0:0:1. The binary bi-stable quantum wire array is respectively crystallized from xanthine-based liquid ingredients at the molar mixture ratios of (verapamil:isoprenaline: superoxide dismutase:adenosine triphosphate) according to (i) 1:1:0:0; (ii) 1:0:1:0; (iii) 1:0:0:1; (iv) 0:1:1:0; (v) 0:1:0:1; and (vi) 0:0:1:1. The ternary bi-stable quantum wire array is respectively crystallized from xanthine-based liquid ingredients at the molar mixture ratios of (verapamil:isoprenaline:superoxide dismutase:adenosine triphosphate) according to (i) 1:1:1:0; (ii) 1:1:0:1; (iii) 1:0:1:1; and (iv) 0:1:1:1. The quaternary bi-stable quantum wire array is respectively crystallized from xanthine-based liquid ingredients at the molar ratios of (verapamil:isoprenaline: superoxide dismutase:adenosine triphosphate) according to (i) 1:1:1:1; (ii) 1:2:2:2; (iii) 1:3:3:3; (iv) 2:1:2:3; (v) 2:2:3:1; (vi) 2:3:1:2; (vii) 3:1:3:2; (viii) 3:2:1:3; and (ix) 3:3:2:1. All unitary, binary, ternary and quaternary nanomedicine are respectively combined with xanthine at a desired molar concentration.

In another aspect of the invention, a crystallized process of preparing a bi-stable quantum wire array includes the following steps: (a) respectively making a pharmaceutical standard solution comprising one or more ingredients selected from the group consisting of verapamil, isoprenaline, superoxide dismutase, and adenosine triphosphate and respectively immersing a substrate into a desired volume of an optimum pharmaceutical standard solution in combination with a desired molar concentration of xanthine solution at $-4°$ C. for 96 hours according to the $L_{16}$ $(2)^{15}$ and $L_9$ $(3)^4$ optimum design protocols, wherein such a time period with a cooling process allows liquid ingredients to be crystallized onto the substrates; (b) cooling verapamil in a range of about 20 zeptoMol to about 0.001 zeptoMol, isoprenaline in a range of about 210 zeptoMol to about 0.001 zeptoMol, adenosine triphosphate in a range of about 260 zeptoMol to about 1 zeptoMol, superoxide dismutase in a range of about 1 zeptoMol to about 0.001 zeptoMol and xanthine in a range of about 50 μM to about 5 mM at $-4°$ C. for 96 hours respectively, resulting in nanometer scale, size-controlled, well-distributed, vertical-patterned bi-stable quantum wire arrays with qubits and kondo effects.

The details of one or more embodiments of the invention are set forth in the accompanying drawings and the description below. Other features, objects, and advantages of the invention will be apparent from the description and drawings, and from the claims.

DESCRIPTION OF DRAWINGS

The patent or application file contains at least one drawing executed in color. Copies of this patent or patent application publication with color drawings will be provided by the Office upon request and payment of the necessary fee.

DETAILED DESCRIPTION

Figure 1:
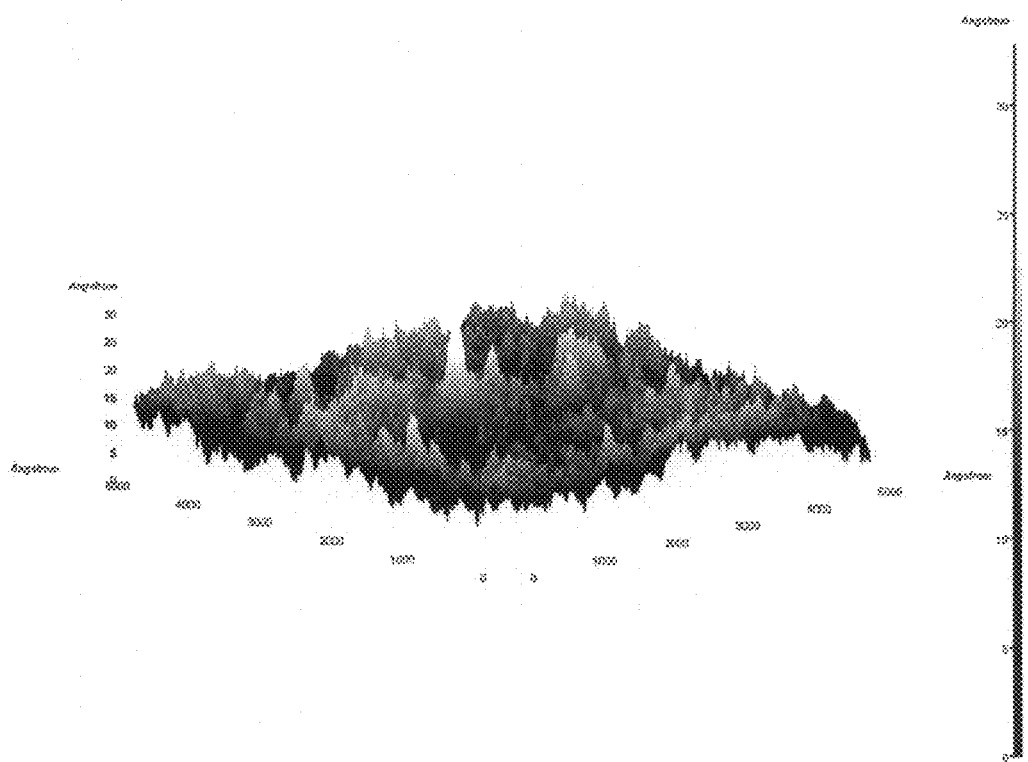
FIG. 1. The PCI (conducting atomic force microscopy, C-AFM) images the self-assembled topographic structure of xanthine-based vertical binary bi-stable quantum wire arrays made from nano-medicine on the N-doped silicon chip, and its cigar-shaped spatial geometrical size covers a height 3 nm, a length 500 nm and wideness 500 nm space, as depicted in FIG. 1.
Figure 2:
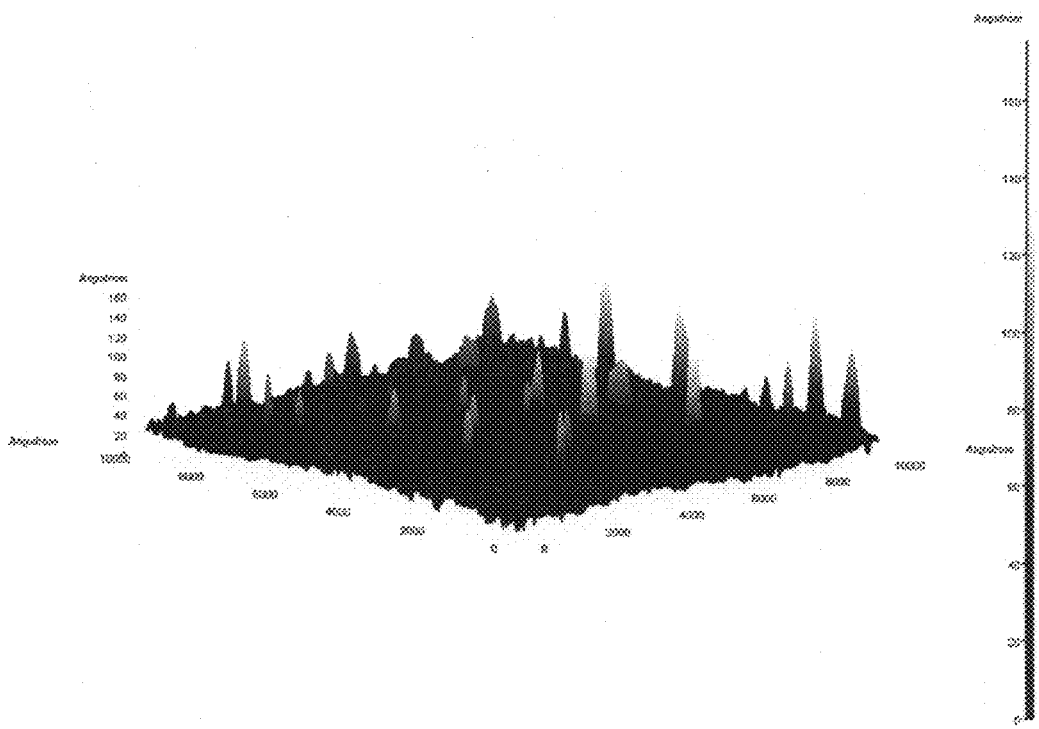
FIG. 2. The PCI (C-AFM) images the self-assembled topographic structure of xanthine-based vertical ternary nanomedicine quantum wires with the highest qubits up to $254\frac{1}{2}\pi$ and $127\pi$ electron spins on the N-doped silicon chip, and its cigar-shaped spatial geometrical size covers a height 16 nm, a length 1000 nm and wideness 1000 nm, as depicted in FIG. 2.
Figure 3:
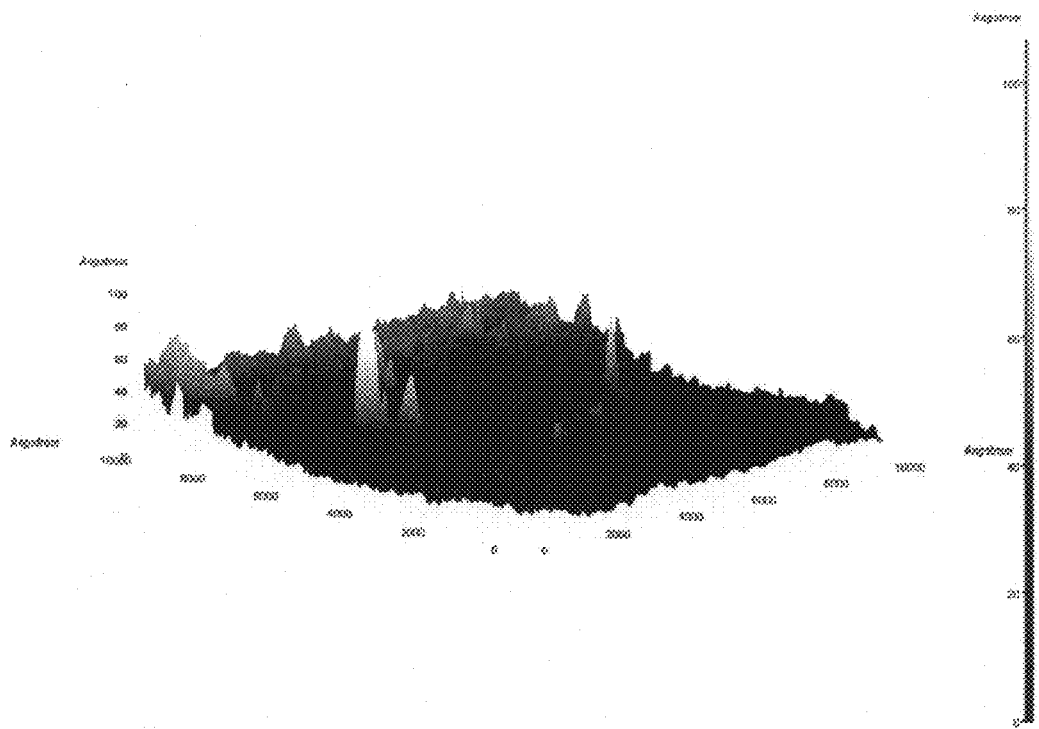
FIG. 3. The PCI (C-AFM) images the self-assembled topographic structure of xanthine-based vertical quinary nanomedicine quantum wires and thin films with non-volatile qubits on the P-doped silicon chip, and its cigar-shaped spatial geometrical size covers a height 10 nm, a length 1000 nm and wideness 1000 nm, as depicted in FIG. 3.
Figure 4:
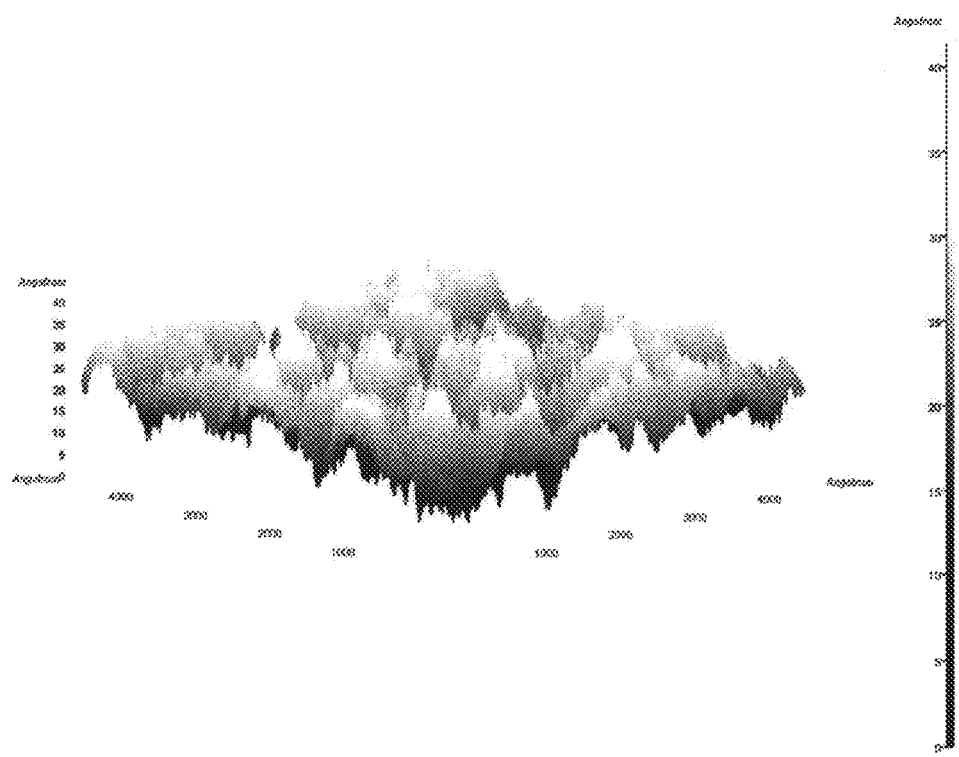
FIG. 4. The PCI (C-AFM) images the self-assembled topographic structure of xanthine-based vertical quinary nanomedicine quantum wires and thin films with the optimum qubits up to $906\frac{1}{2}\pi$, $302\pi$ or $151(2\pi)$ electron spins on the P-doped silicon chip, and its cigar-shaped spatial geometrical size covers a height 4 nm, a length 400 nm and wideness 400 nm, as depicted in FIG. 4.
Figure 5:
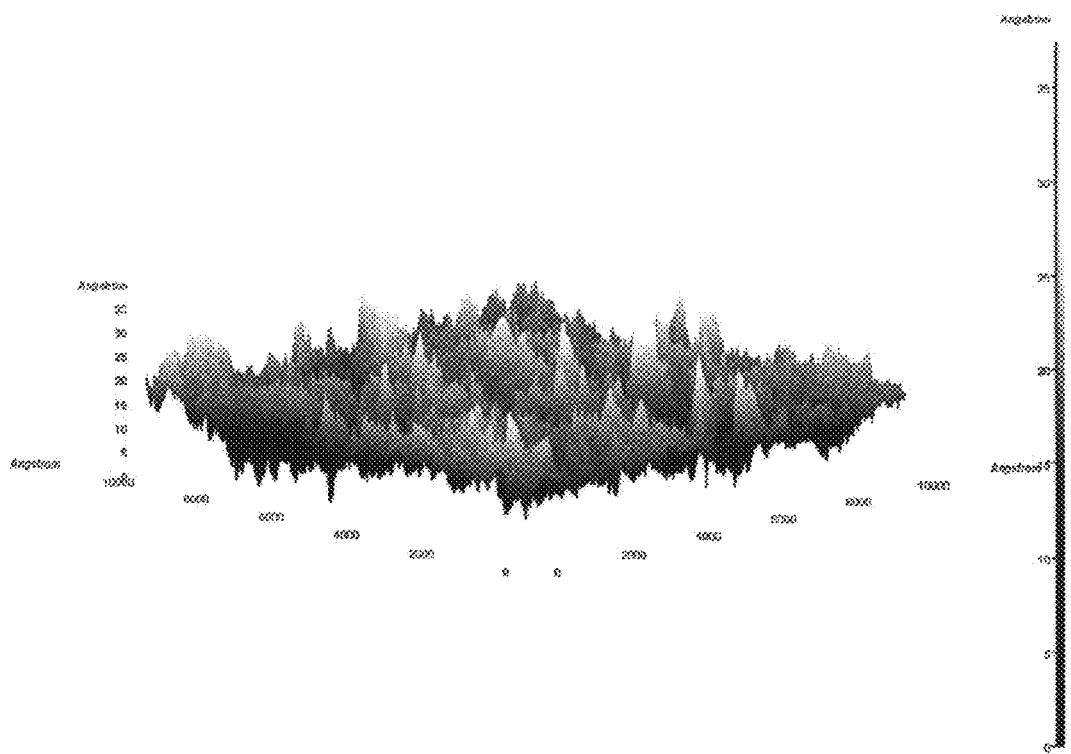
FIG. 5. The PCI (C-AFM) images the self-assembled topographic structure of xanthine-based vertical quinary nanomedicine quantum wires and thin films with the controllable qubits with the phases of initial zero, $\frac{1}{2}\pi$, $\pi$ and $2\pi$ electron spins on the P-doped silicon chip, and its cigar-shaped spatial geometrical size covers a height 3.5 nm, a length 1000 nm and wideness 1000 nm, as depicted in FIG. 5.
Figure 6:
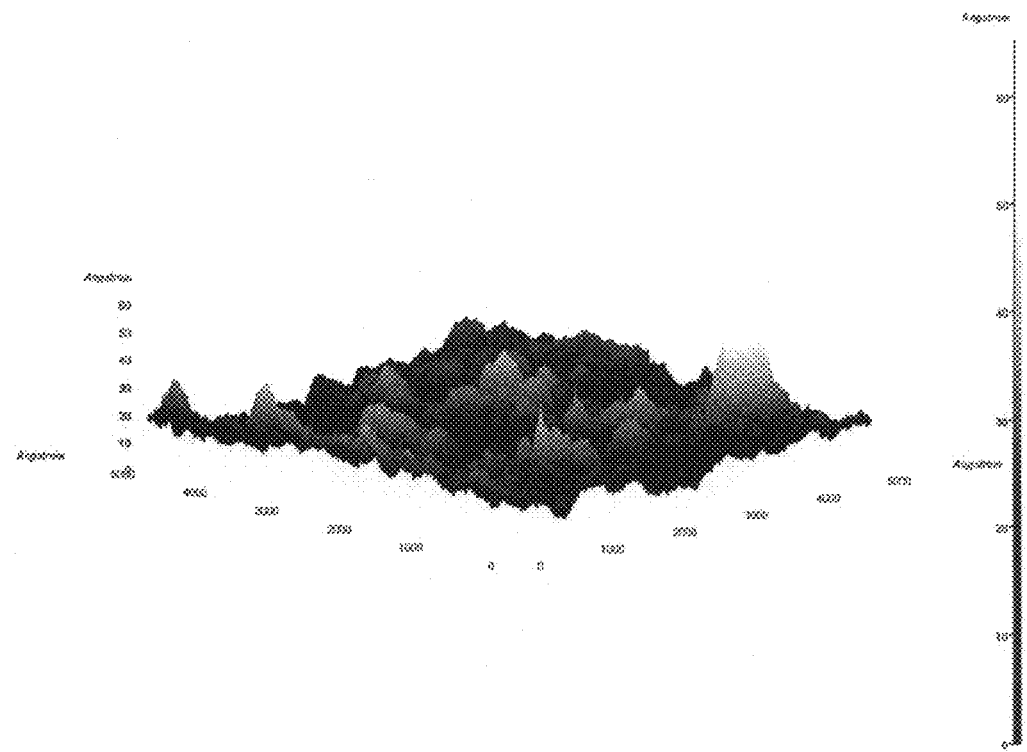
FIG. 6. The PCI (C-AFM) images the self-assembled topographic structure of xanthine-based vertical quinary nanomedicine quantum wires and thin films with the controllable qubits with the phases of initial zero, $\frac{1}{2}\pi$, $\pi$ and $1\frac{1}{2}\pi$ electron spins on the P-doped silicon chip, its cigar-shaped spatial geometrical size covers a height 6 nm, a length 500 nm and wideness 500 nm, as depicted in FIG. 6.
Figure 7:
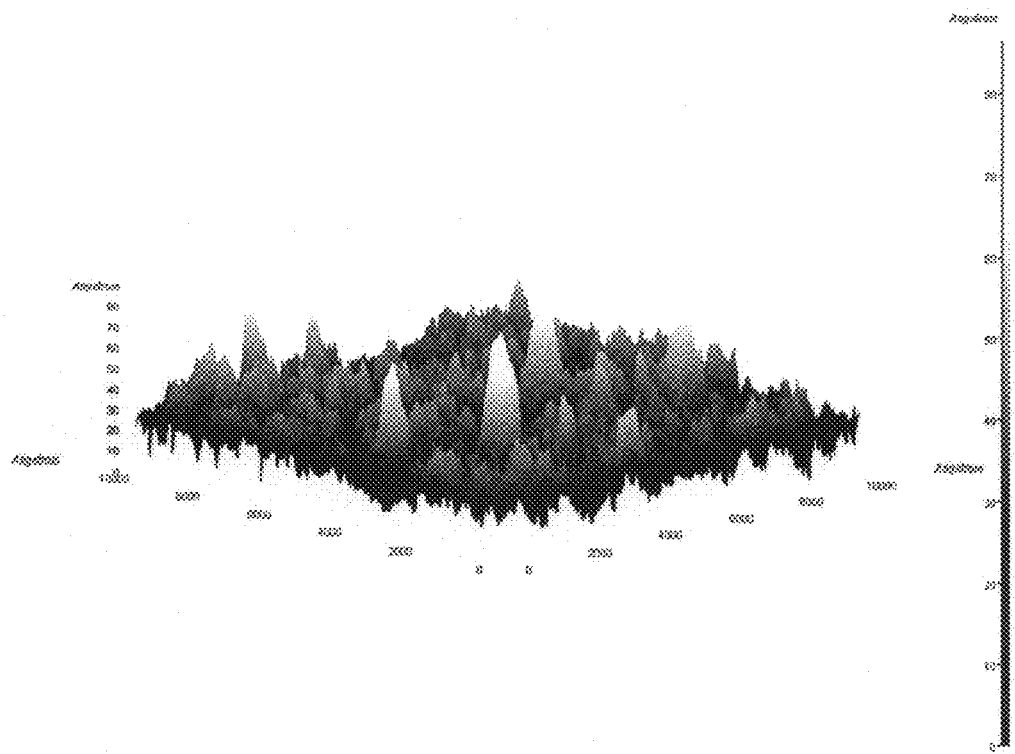
FIG. 7. The PCI (C-AFM) images the self-assembled topographic structure of xanthine-based vertical quinary nanomedicine quantum wires and thin films with the ±10V bias potential-initiated qubits on the P-doped silicon chip, and its cigar-shaped spatial geometrical size covers a height 8 nm, a length 1000 nm and wideness 1000 nm, as depicted in FIG. 7.
Figure 8:
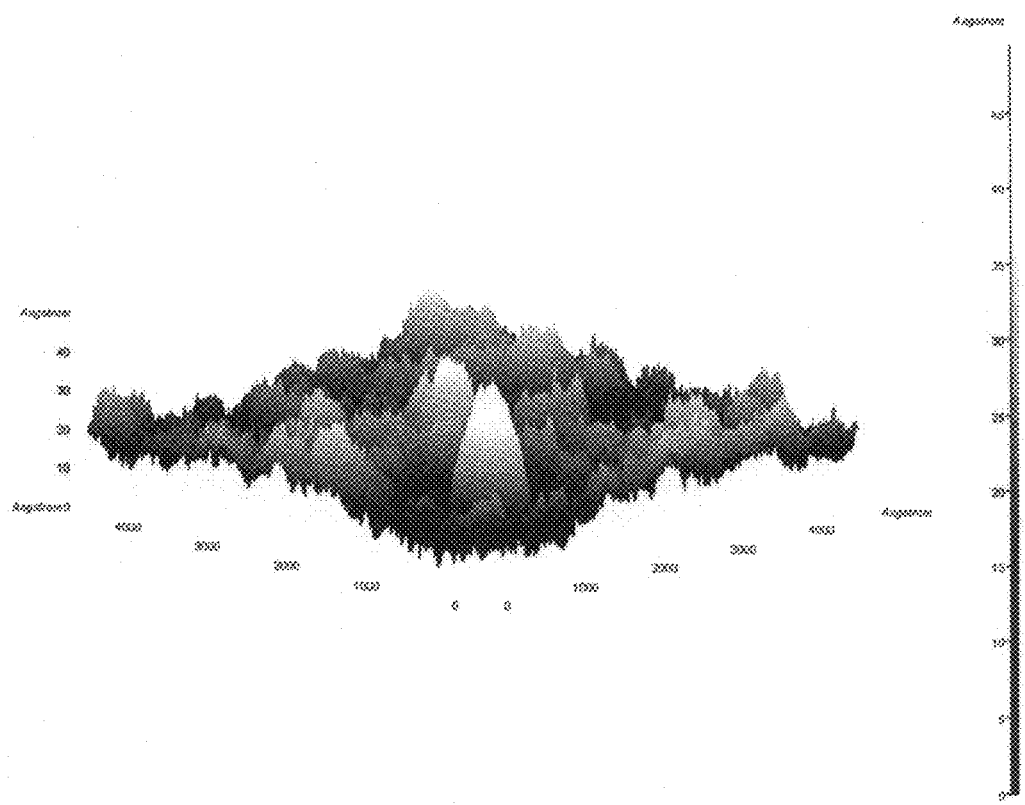
FIG. 8. The PCI (C-AFM) images the self-assembled topographic structure of xanthine-based vertical quinary nanomedicine quantum wires and thin films with the ±7V and ±9V bias potential-initiated zero $-\frac{1}{2}\pi-\pi$ and zero-$\frac{1}{2}\pi$-$2\pi$ electron spin phase transitions on the P-doped silicon chip, its cigar-shaped spatial geometrical size covers a height 4 nm, a length 400 nm and wideness 400 nm, as depicted in FIG. 8.
Figure 9:
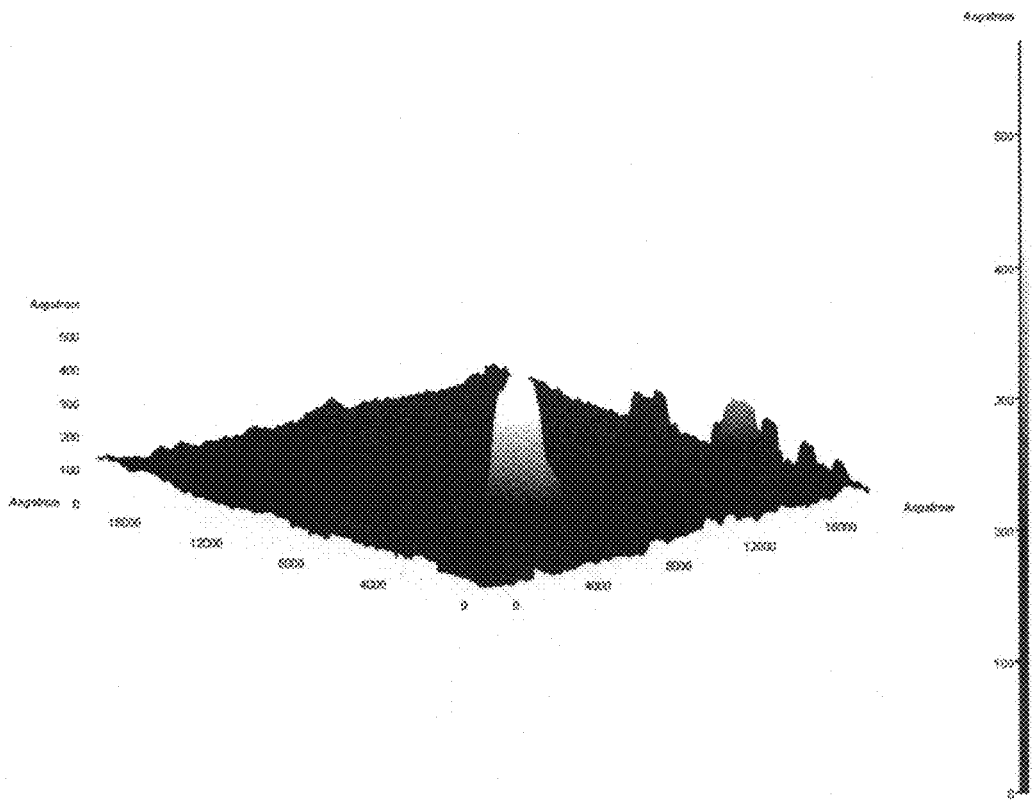
FIG. 9. The PCI (C-AFM) images the self-assembled topographic structure of xanthine-based vertical quinary nanomedicine quantum wires and thin films with the ±7V, ±8V and ±9V bias potential-initiated $\pi$-$\frac{1}{2}\pi$-$2\pi$ and zero-$\frac{1}{2}\pi$-$2\pi$ electron spin phase transitions on the P-doped silicon chip, and its cigar-shaped spatial geometrical size of a height 50 nm, a length 1600 nm and wideness 1600 nm, as depicted in FIG. 9.
Figure 10:
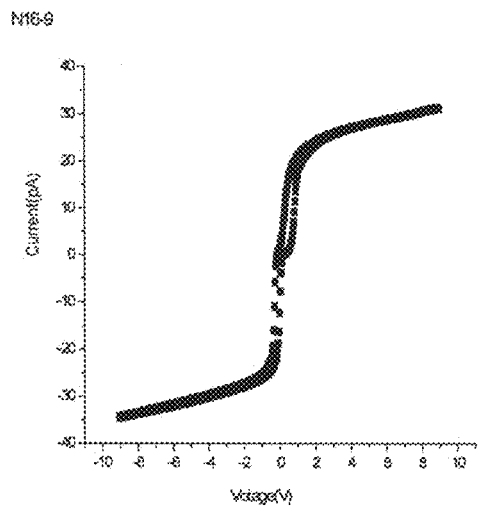
FIG. 10. The PCI (C-AFM) measures the I-V curve of ±35 pA quantum tunneling hysteresis (a, X axis=Voltage, Y axis=Current), the kondo effect conductance spectrum of 140 pA/V maximum differential conductance peak at 0 bias potential (b, X axis=Voltage, Y axis=Conductance), the energy-frequency-phase spectrum (c, X axis=Frequency, Y axis=Phase, Z axis=Energy) and the energy-time-phase spectrum (d, X axis=Time, Y axis=Phase, Z axis=Energy) of ±2V bias potential-initiated electron spins for qubits, all of them correspond to FIG. 1.
Figure 10:
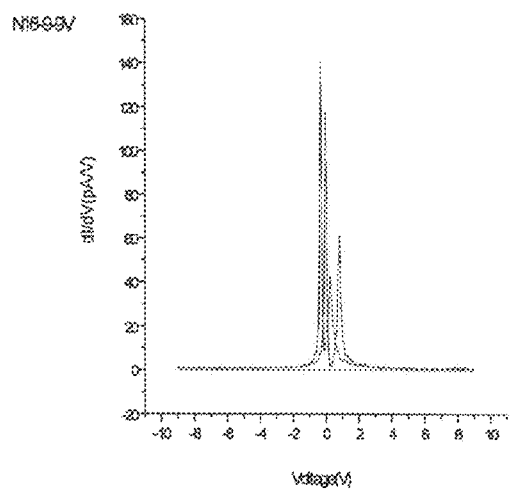
Figure 10:
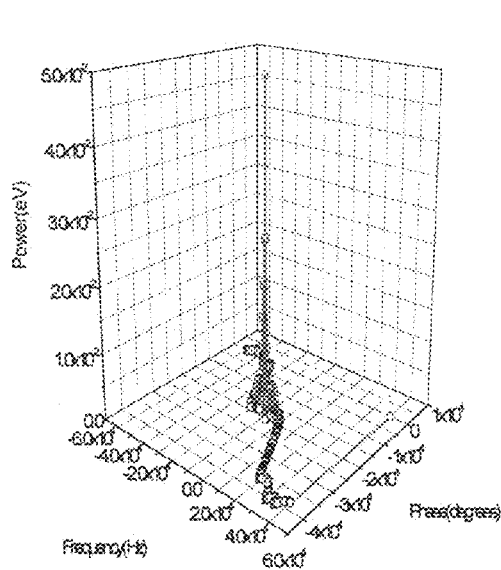
Figure 10:
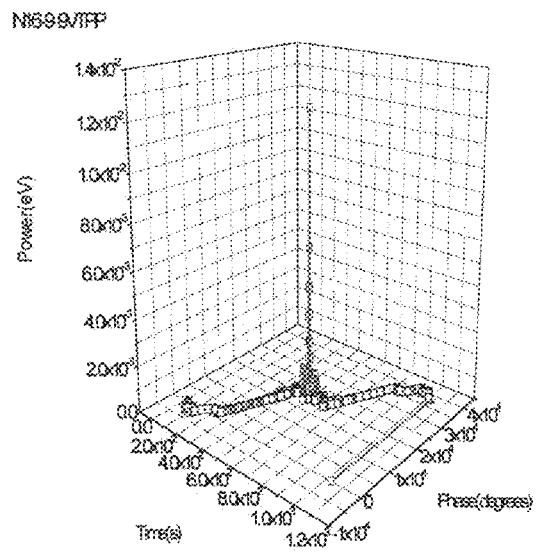
Figure 11:
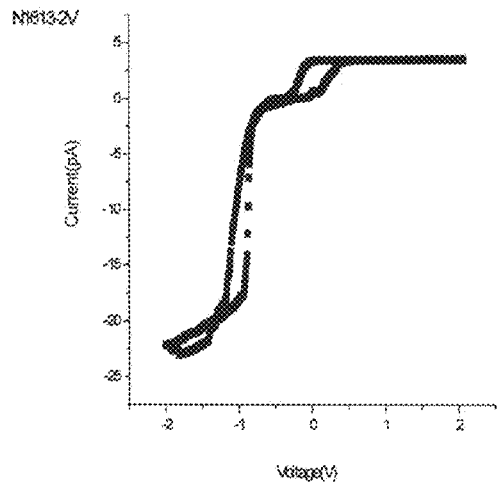
FIG. 11. The PCI (C-AFM) measures the I-V curve of 2.5 pA~-22.5 pA quantum tunneling hysteresis (a, X axis=Voltage, Y axis=Current), the kondo effect conductance spectrum of 325 pA/V maximum differential conductance peak at -1V bias potential (b, X axis=Voltage, Y axis=Conductance), the energy-frequency-phase spectrum (c, X axis=Frequency, Y axis=Phase, Z axis=Energy) and the energy-time-phase spectrum (d, X axis=Time, Y axis=Phase, Z axis=Energy) of ±9V bias potential-initiated 954½π and 477π electron spins for dynamics of qubits, all of them correspond to FIG. 2.
Figure 11:
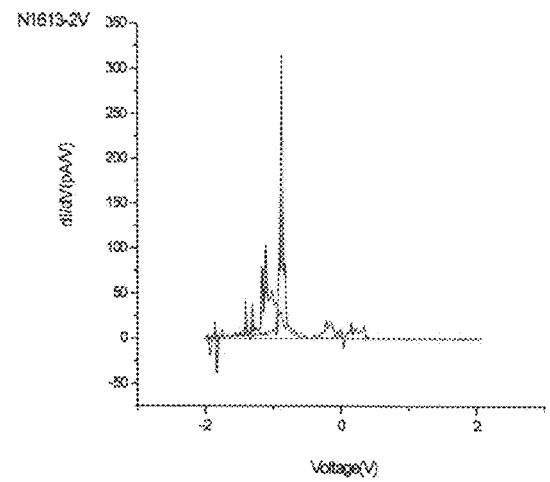
Figure 11:
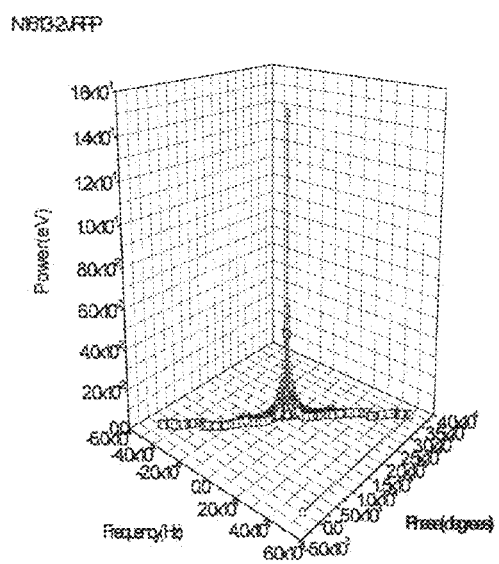
Figure 11:
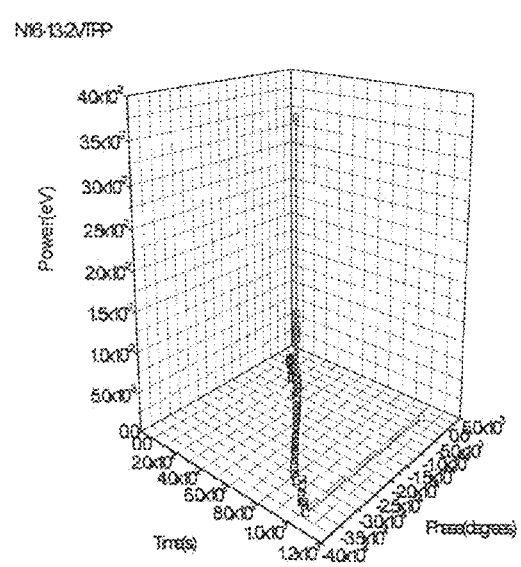
Figure 12:
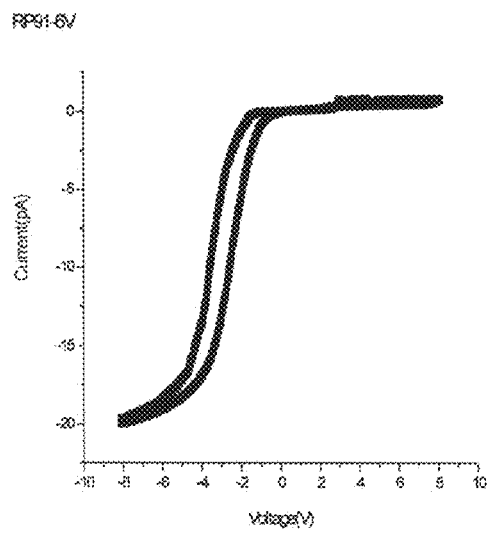
FIG. 12. The PCI (C-AFM) measures the I-V curve of 0 pA~-20 pA quantum tunneling hysteresis and quantum Hall effect (a, X axis=Voltage, Y axis=Current), the kondo effect conductance spectrum of 13 pA/V maximum differential conductance peak at -4V bias potentials (b, X axis=Voltage, Y axis=Conductance), the energy-frequency-phase spectrum (c, X axis=Frequency, Y axis=Phase, Z axis=Energy) and the energy-time-phase spectrum (d, X axis=Time, Y axis=Phase, Z axis=Energy) of ±6V, ±8V, ±9V and ±10V bias potential-initiated non-volatile qubits, all of them correspond to FIG. 3.
Figure 12:
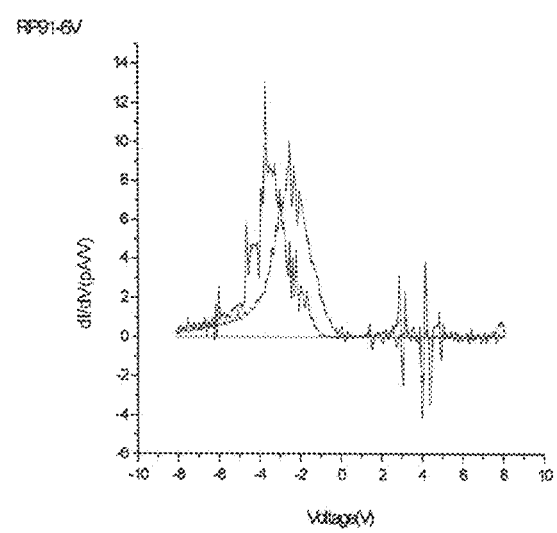
Figure 12:
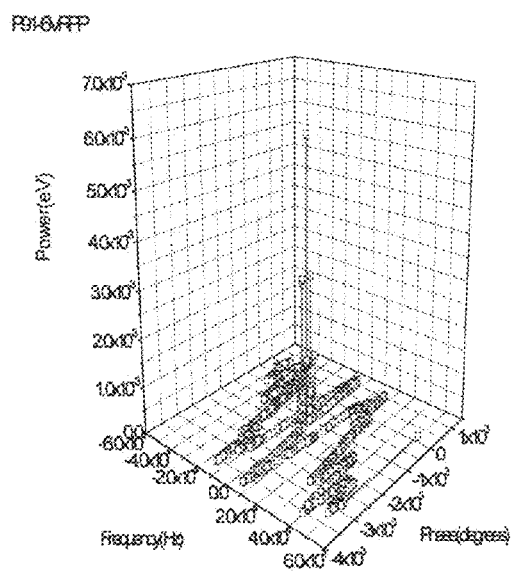
Figure 12:
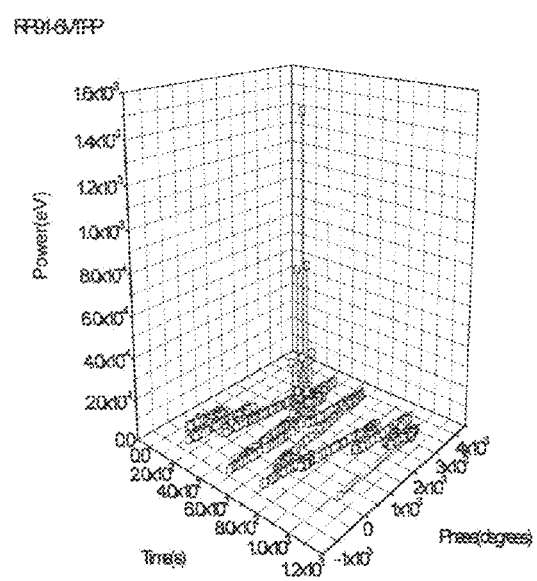
Figure 13:
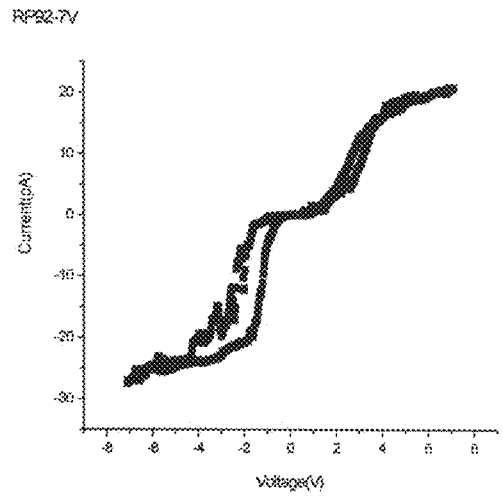
FIG. 13. The PCI (C-AFM) measures the I-V curve of ±30 pA quantum tunneling hysteresis and 0 pA quantum Hall effect (a, X axis=Voltage, Y axis=Current), the kondo effect conductance spectrum of 100 pA/V maximum differential conductance peak at -2V bias potentials (b, X axis=Voltage, Y axis=Conductance), the energy-frequency-phase spectrum (c, X axis=Frequency, Y axis=Phase, Z axis=Energy) and the energy-time-phase spectrum (d, X axis=Time, Y axis=Phase, Z axis=Energy) of ±7V, ±8V, ±9V and ±10V bias potential-initiated ½π-π electron spin shuttling for qubits, all of them correspond to FIG. 4.
Figure 13:
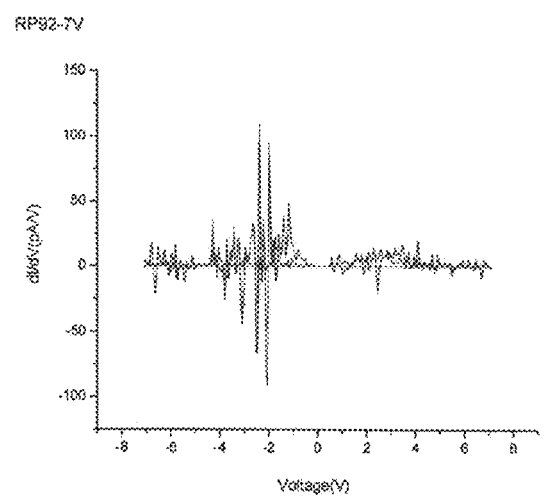
Figure 13:
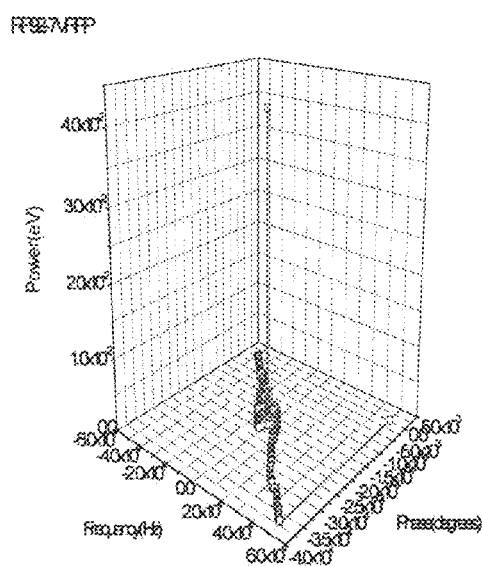
Figure 13:
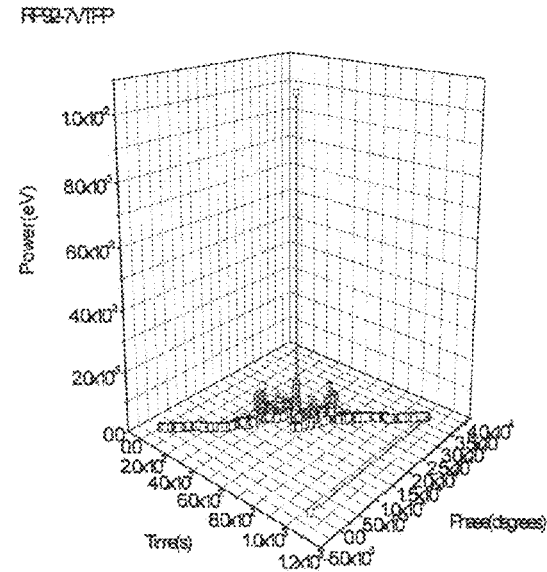
Figure 14:
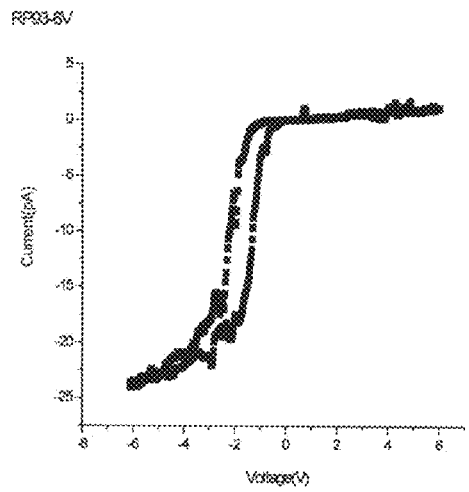
FIG. 14. The PCI (C-AFM) measures the I-V curve of 0 pA~-25 pA quantum tunneling hysteresis and quantum Hall effect (a, X axis=Voltage, Y axis=Current), the kondo effect conductance spectrum of 70 pA/V~-50 pA/V maximum differential conductance peak at -2V bias potentials (b, X axis=Voltage, Y axis=Conductance), the energy-frequency-phase spectrum (c, X axis=Frequency, Y axis=Phase, Z axis=Energy) and the energy-time-phase spectrum (d, X axis=Time, Y axis=Phase, Z axis=Energy) of ±6V, ±7V, ±8V, ±9V and ±10V bias potential-initiated zero-½π-2π electron spin shuttling for qubits, all of them correspond to FIG. 5.
Figure 14:
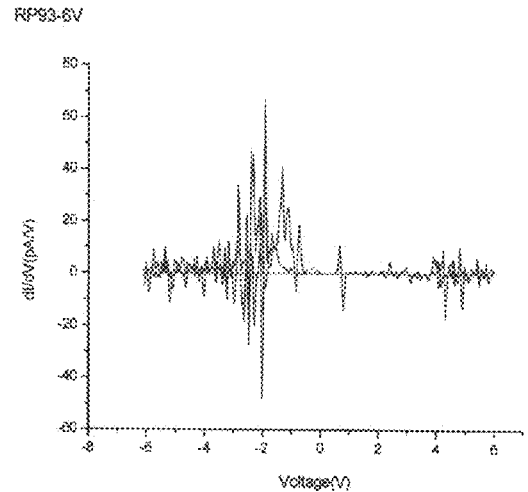
Figure 14:
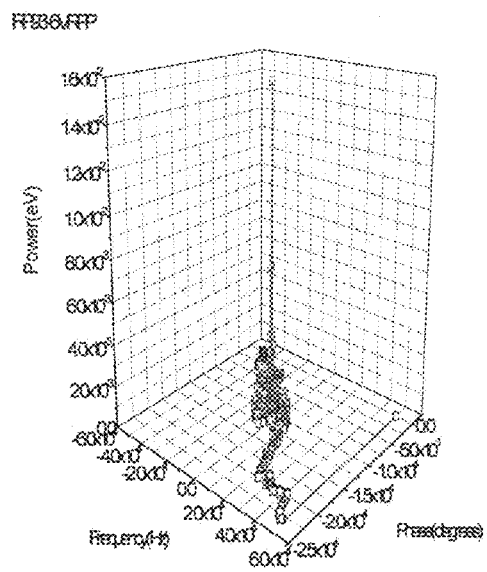
Figure 14:
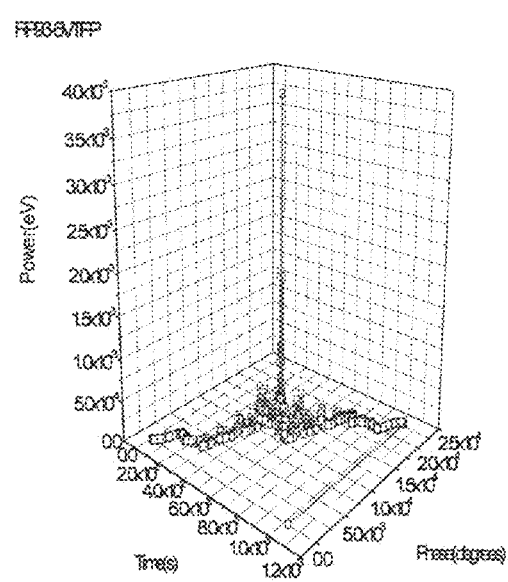

Vertical bi-stable quantum wire arrays are prepared from liquid unitary, binary, ternary, and quaternary nanomedicine complexes described herein to co-crystallized patterns through an interaction of inelastic electron tunneling and intermolecular co-ordinations of an antioxidase antioxidant, agonists of β-adrenergic and $P_2$ purinergic receptors, and/or a phenylalkylamine (benzalkonium) calcium channel blocker.

Crystallized, nanometer scale, size-controllable, vertical bi-stable quantum wire arrays with well-aligned, discrete-distributed spatial geometrical order structure array patterns are prepared from advantageous liquid ingredients of isoprenaline in a range of about 210 zeptoMol to about 0.001 zeptoMol, adenosine triphosphate in a range of about 260 zeptoMol to about 1 zeptoMol, verapamil in a range of about 20 zeptoMol to about 0.001 zeptoMol, and/or superoxide dismutase in a range of about 1 zeptoMol to about 0.001 zeptoMol, all of above unitary, binary, ternary and/or quaternary ingredients are combined with 50 μM~5 mM xanthine in a liquid phase.

A nanometer preparation process of vertical bi-stable quantum wire arrays employs an interaction of inelastic electron tunneling and intermolecular electrostatic co-ordination to self-assemble optimum xanthine-based unitary, binary, ternary, and quaternary pharmaceutical standard solutions of isoprenaline, verapamil, superoxide dismutase, and/or adenosine triphosphate according to the $L_{16}(2)^{15}$ and the $L_9(3)^4$ orthogonal design protocols. The nanometer scale spatial vertical geometrical architecture self-assembly approach is advantageous for developing mechanism-based multi-functional nano-devices, ultra-faster, ultra-sensitive, ultra-density qubit devices and nano-diagnostic tools towards clinical utilities, and for developing biocompatible, mechanism-targeted, ultra-fine, ultra-sensitive nanometer scale sensors, and electron spin-based qubit devices competent for liquid phase working and clinical uses.

The electronic feature of vertical bi-stable quantum wire arrays is bi-stable electrical hysteresis with qubits (a relatively higher current level and a relatively lower current level) in the current-voltage (I-V) curves and quantum resonance (kondo effects) in their first derivatives of I-V curves (the dI-dV conductance spectrum) at room temperature. Kondo effects can be identified by a maximum conductance peak around zero bias potential in the $1^{st}$ derivative of I-V curves at room temperature (a room temperature Kondo effect is a quantum resonance phenomenon), and a feature of qubits can be identified by the energy-frequency-phase and energy-time-phase spectra after the faster Fourier transformation of the dI-dV conductance spectrum in frequency and time domains respectively, wherein the velocity uncertain quantum phase transition wave is clearly visible at the absolute zero point in a zero-point motion manner. The symmetry bi-stable spin-up and spin-down qubits undergo $\pm\frac{1}{2}\pi N$ (N may be several hundreds) phase transitions at the central point, whereas non-symmetry spin-up and spin-down qubits undergo spin echo ($\pi$ angular momentum) at an initial and an end phase transition in combination with a non-symmetry spin-up and spin-down phase transition at the central point (presence of several $\frac{1}{2}\pi$ phase transition difference) for qubits. Both of symmetry and non-symmetry phase transitions are in a lower power state around the sub-eV level.

The invention employs combined methods of $L_{16}(2)^{15}$ and $L_9(3)^4$ orthogonal optimization protocols, PCI scanning probe microscopy, i.e., conducting atomic force microscopy (C-AFM), and ORIGIN mathematical analyses (available from OriginLab Co., Northampton, Mass.) to prepare the crystallized patterns from liquid unitary, binary, ternary, quaternary and quinary elements of isoprenaline (a β-adrenergic agonist), adenosine triphosphate (a $P_2$-purinergic agonist), verapamil (a phenylalkylamine calcium channel blocker), superoxide dismutase an antioxidase antioxidant) and xanthine (a nucleic acid) respectively, and identify the advantage feature of vertical bi-stable quantum wire arrays with qubits.

The vertical unitary bi-stable quantum wire arrays on the p-doped (8-12Ω cm) or the n-doped (0.01~0.05Ω cm) silicon substrates comprises xanthine-based unitary liquid pharmaceutical ingredient selected from isoprenaline (β-adrenergic agonist), adenosine triphosphate ($P_2$-purinergic agonist), verapamil (phenylalkylamine calcium channel blocker) or superoxide dismutase (antioxidase antioxidant) at a molar mixture ratio according to (i) 1:0:0:0; (ii) 0:1:0:0; (iii) 0:0:1:0; and/or (iv) 0:0:0:1.

The vertical binary bi-stable quantum wire arrays on the p-doped (8-12Ω cm) or the n-doped (0.01~0.05Ω cm) silicon substrates comprises xanthine-based binary liquid pharmaceutical ingredient selected from isoprenaline (β-adrenergic agonist), adenosine triphosphate ($P_2$-purinergic agonist), verapamil (phenylalkylamine calcium channel blocker) and superoxide dismutase (antioxidase antioxidant) at a molar mixture ratio according to (i) 1:1:0:0; (ii) 1:0:1:0; (iii) 1:0:0:1; (iv) 0:1:1:0; (v) 0:1:0:1 and (vi) 0:0:1:1.

The vertical ternary bi-stable quantum wire arrays on the p-doped (8-12Ω cm) or the n-doped (0.01~0.05Ω cm) silicon substrates comprises xanthine-based ternary liquid pharmaceutical ingredient selection from isoprenaline (a β-adrenergic agonist), adenosine triphosphate (a $P_2$-purinergic agonist), verapamil (a phenylalkylamine calcium channel blocker) and superoxide dismutase (an antioxidase antioxidant) at a molar mixture ratio according to (i) 1:1:1:0; (ii) 1:0:1:1; (iii) 1:1:0:1; and (iv) 0:1:1:1.

The vertical quaternary bi-stable quantum wire arrays on the p-doped (8-12Ω cm) or the n-doped (0.010~0.05Ω cm) silicon substrates comprises xanthine-based quaternary liquid pharmaceutical ingredient selection from isoprenaline (a β-adrenergic agonist), adenosine triphosphate (a $P_2$-purinergic agonist), verapamil (a phenylalkylamine calcium channel blocker) or superoxide dismutase (an antioxidase antioxidant) at a molar mixture ratio according to (i) 1:1:1:1; (ii) 1:2:2:2; (iii) 1:3:3:3; (iv) 2:1:2:3; (v) 2:2:3:1; (vi) 2:3:1:2; (vii) 3:1:3:2; (viii) 3:2:1:3; and (ix) 3:3:2:1.

This invention can generate 24 groups' nanometer scale topographic structure data of size-controlled, discrete-distributed, well-aligned patterns of vertical bi-stable quantum wire arrays and 24 groups' electrical parameters of self-assembled unitary, binary, ternary, quaternary and quinary vertical bi-stable quantum wire arrays with qubits, namely, I-V curves, their first derivatives (the dI-dV conductance spectra) and faster Fourier transformations in frequency and time domains (the energy-frequency-phase spectra and the energy-time-phase spectra) and the three-dimensional (3D) topographic structures of bi-stable vertical quantum wire arrays can be respectively identified by C-AFM images and C-AFM electrical property measurements as depicted in FIGS. 1-18. The spatial sizes of vertical bi-stable quantum wire arrays may range from angstroms to nanometers of several tens. The shortest vertical bi-stable quantum wire array is in a range of 14 angstroms. The smallest spatial size of a vertical bi-stable quantum wire array pattern is a range of 2 angstroms.

The architecture feature of vertical bi-stable quantum wire arrays is geometrical regular shape, size-controllable intermolecular coordination patterns, as shown in FIGS. 1-9. The electrical feature of bi-stable quantum wire arrays includes electrical hysteresis, quantum tunneling currents, kondo effects and symmetry or non-symmetry spin-up and spin-down qubits in a lower power state, as typically identified in FIGS. 10*a-d*, 11*a-d*, 12*a-d*, 13*a-d*, 14*a-d*, 15*a-d*, 16*a-d*, 17*a-d* and 18*a-d*. The topographic structure and electrical features of vertical bi-stable quantum wire arrays may be advantageous for developing multi-functional nano-diagnosis device and qubit informatics devices.

The process of preparing vertical bi-stable vertical quantum wire arrays on the silicon substrates includes the following steps as: 1) respectively preparing liquid pharmaceutical ingredients according to pharmaceutical standard guidelines; 2) respectively preparing liquid pharmaceutical standard ingredients of verapamil hydrochloride, isoprenaline hydrochloride, superoxide dismutase, and adenosine triphosphate in the desired concentrations as mentioned in [0006]; and 3) respectively mixing the liquid pharmaceutical standard ingredients of verapamil hydrochloride, isoprenaline hydrochloride, superoxide dismutase, and adenosine triphosphate in combination with a given molar concentration of xanthine buffer solution as indicated in [0006] in the given volume of buffer solutions at room temperature; 4) respectively storing the above liquid ingredients at −4° C. for applications; 5) respectively immersing the p-doped (8-12Ω cm) or the n-doped (0.01~0.05Ω cm) silicon chips into the above desired xanthine-based unitary, binary, ternary and quaternary pharmaceutical ingredient solutions according to $L_{16}(2)^{15}$ and $L_9(3)^4$ orthogonal design protocols as described in [0006]; and 6) respectively storing liquid ingredients onto the p-doped (8-12Ω cm) or the n-doped (0.01~0.05Ω cm) silicon substrates at −4° C. for 96 hours to obtain a liquid-solid phase transition and result in well-aligned and uniformly distributed vertical bi-stable quantum wire arrays with qubits and kondo effects.

In the $L_{16}(2)^{15}$ orthogonal design protocol, there are four independent unitary pharmaceutical ingredient groups, six independent binary pharmaceutical ingredient groups, four independent ternary pharmaceutical ingredient groups and one independent quaternary pharmaceutical ingredient group at two molar ratios plus a blank control group. In the $L_9(3)^4$ orthogonal design protocol, there are nine quaternary pharmaceutical ingredient groups at three molar ratios. All of above pharmaceutical ingredients are respectively combined with xanthine at given molar concentrations as announced in [0006].

Example 1

Liquids Pharmaceutical ingredients were respectively prepared according to the pharmaceutical standards. Reference may be made to pharmaceutical standard guideline issued by the Ministry of Health in China. Topographic structure and qubit features of the 1:1:1:1 molar mixture ratios obtained from Example 1 are depicted in FIGS. 3 and 12a-d.

The following pharmaceutical solutions were prepared according to the pharmaceutical standards (reference may be made to pharmaceutics guideline of the ministry of health in China):
  i. Preparing a verapamil hydrochloride pharmaceutical liquid at a concentration of 2.5 mg/5 mL.
  ii. Preparing an isoprenaline hydrochloride pharmaceutical liquid at a concentration of 2 mg/100 mL.
  iii. Preparing a physiological buffer solution of superoxide dismutase at a concentration of 1 mg/2 mL.
  iv. Preparing a physiological buffer solution of adenosine triphosphate at a concentration of 20 mg/3.3 mL.
  v. Respectively preparing and taking the optimum molecular numbers from each ingredients of verapmil in a range of about 20 zeptoMol to about 0.001 zeptoMol, isoprenaline in a range of about 210 zeptoMol to about 0.001 zeptoMol, superoxide dismutase in a range of about 1 zeptoMol to about 0.001 zeptoMol, adenosine triphosphate in a range of 260 zeptoMol to about 1 zeptoMol and xanthine in a range of about 50 μM to about 5 mM, respectively mixing them at room temperature and preparing xanthine-based quaternary pharmaceutical ingredient physiological buffer solutions at a molar mixture ratio of 1:1:1:1 (verapamil:isoprenaline:superoxide dismutase:adenosine triphosphate) according to the $L_9(3)^4$ orthogonal design protocol at room temperature, respectively keeping the final volume of 1 mL xanthine-based quaternary pharmaceutical ingredient physiological buffer solutions at −4° C. for applications.
  vi. Immersing a p-doped silicon substrate (8-12Ω cm) ed into the above desired 1 mL xanthine-based 1:1:1:1 (verapamil:isoprenaline:superoxide dismutase:adenosine triphosphate) quaternary pharmaceutical ingredient physiological buffer solutions according to the $L_9(3)^4$ orthogonal design protocol, and storing at −4° C. for 96 hours.
  vii. The results of this practice example showed that the height of a quantum wire array is 10 nm (FIG. 3); the I-V curve presented a bi-stable current peaks of 0.813 pA and −19.95 pA within ±8V bias potentials (FIG. 12a), the differential conductance spectrum (dI/dV) revealed the quantized kondo effect, i.e., the maximum conductance peak of 13.08854 pA/V at the −3.741V bias potential (FIG. 12b), the phase transitions covered zero degrees to −1260 degrees within the frequency domain from ±50000 Hz to 7.2475E-12 Hz in the frequency-phase-energy spectrum (FPP), where 14(−½π) electron spins or 7(−π) spin echo occurred at the y axis with the central frequency of 7.2475E-12 Hz at the x-axis and the energy fluctuation of 0.00603 eV at the z axis (FIG. 12c), the phase transitions swept from zero degree to 1260 degrees within the time domain from zero to 1000 μs in the time-phase-energy spectrum (TPP),where 14(½π) electron spins or 7(π) spin echo occurred at the y axis with the central time of 513 μs at the x-axis and the energy fluctuation of 0.00151 eV at the z axis (FIG. 12d); the parental data in the FIG. 12(c-d) simultaneously revealed ±(½π) N electron spins-driven qubits.

Example 2

Liquid pharmaceutical ingredients were prepared according to the pharmaceutical standards (reference may be made to pharmaceutical standard guideline issued by the Ministry of Health in China). Topographic structure and qubit features of the 1:2:2:2 molar mixture ratios obtained from Example 2 are depicted in FIGS. 4 and 13a-d.

The following pharmaceutical solutions were prepared according to the pharmaceutical standards, which may refer to pharmaceutics guideline of the ministry of health in China:
  i. Preparing a verapamil hydrochloride pharmaceutical liquid at a concentration of 2.5 mg/5 mL.
  ii. Preparing an isoprenaline hydrochloride pharmaceutical liquid at a concentration of 2 mg/100 mL.
  iii. Preparing a physiological buffer solution of superoxide dismutase at a concentration of 1 mg/2 mL.
  iv. Preparing a physiological buffer solution of adenosine triphosphate at a concentration of 20 mg/3.3 mL.
  v. Respectively preparing and taking the optimum molecular numbers from each ingredients of verapmil in a range of about 20 zeptoMol to about 0.001 zeptoMol, isoprenaline in a range of about 210 zeptoMol to about 0.001 zeptoMol, superoxide dismutase in a range of about 1 zeptoMol to about 0.001 zeptoMol, adenosine triphosphate in a range of 260 zeptoMol to about 1 zeptoMol and xanthine in a range of about 50 μM to about 5 mM, respectively mixing them at room temperature and preparing xanthine-based quaternary pharmaceutical ingredient physiological buffer solutions at molar mixture ratios of 1:2:2:2 (verapamil:isoprenaline:superoxide dismutase:adenosine triphosphate), mixing them at room temperature according to the $L_9(3)^4$ orthogonal design protocol, respectively keeping the 1 mL final volume of xanthine-based quaternary pharmaceutical ingredient physiological buffer solutions at −4° C. for applications.

vi. Immersing a p-doped silicon substrate (8-12Ω cm) into the above desired 1 mL xanthine-based 1:2:2:2 (verapamil:isoprenaline:superoxide dismutase:adenosine triphosphate) quaternary pharmaceutical ingredient physiological buffer solutions according to the $L_9$ $(3)^4$ orthogonal design protocol, and storing at −4° C. for 96 hours.

vii. The results of this practice example profiled that the height of quantum wire array is 4 nm (FIG. 4); the I-V curve presented a bi-stable electrical property, i.e., the higher current of 20.71 pA and the lower current of −27.053 pA occurred within the ±7V bias potentials (FIG. 13a); the differential conductance spectrum (dI/dV) revealed the quantized kondo effect, i.e., the maximum conductance peak of 110.492 pA/V located at the −2.376V bias potential (FIG. 13b); the frequency-phase-energy spectrum (FPP) showed phase transitions from 180 degrees to −18180 degrees within the frequency domain from ±50000 Hz to 7.2475E-12 Hz, where 99(−½π) or 33(−1½π) or 404(−¼π) typical electron spins occurred at the y axis with the central frequency of 7.2475E-12 Hz at the x axis and the energy fluctuation of 0.04216 eV (FIG. 13c); the time-phase-energy spectrum (TPP) presented phase transitions from zero degree to 18540 degrees within the time domain from 0 μs to 100 μs, where 906(½π) or 302(1½π) or 412(¼π) typical electron spins happened at the y axis with the central time of 513 μs at the x axis and the energy fluctuation of 0.010541 eV at the z axis (FIG. 13d). The parental data in FIG. 13c-d simultaneously revealed ±(½π) N, ±(¼π) N and ±(1½π) N typical electron spins-driven qubits.

Example 3

Liquid pharmaceutical ingredients were prepared according to the pharmaceutical standards. Reference may be made to pharmaceutical standard guideline issued by the Ministry of Health in China. Topographic structure and qubit features of the 1:3:3:3 molar mixture ratios obtained in Example 3 are depicted in FIGS. 5 and 14a-d.

The following pharmaceutical solutions were prepared according to the pharmaceutical standards, which may refer to pharmaceutics guideline of the ministry of health in China:

i. Preparing a verapamil hydrochloride pharmaceutical liquid at a concentration of 2.5 mg/5 mL.

ii. Preparing an isoprenaline hydrochloride pharmaceutical liquid at a concentration of 2 mg/100 mL.

iii. Preparing a physiological buffer solution of superoxide dismutase at a concentration of 1 mg/2 mL.

iv. Preparing a physiological buffer solution of adenosine triphosphate at a concentration of 20 mg/3.3 mL.

v. Respectively preparing and taking the optimum molecular numbers from each ingredients of verapmil in a range of about 20 zeptoMol to about 0.001 zeptoMol, isoprenaline in a range of about 210 zeptoMol to about 0.001 zeptoMol, superoxide dismutase in a range of about 1 zeptoMol to about 0.001 zeptoMol, adenosine triphosphate in a range of 260 zeptoMol to about 1 zeptoMol and xanthine in a range of about 50 μM to about 5 mM, respectively mixing them at room temperature and preparing xanthine-based quaternary pharmaceutical ingredient physiological buffer solutions at molar mixture ratios of 1:3:3:3 (verapamil:isoprenaline:superoxide dismutase:adenosine triphosphate), mixing them at room temperature according to the $L_9$ $(3)^4$ orthogonal design protocol, respectively keeping the 1 mL final volume of xanthine-based quaternary pharmaceutical ingredient physiological buffer solutions at −4° C. for applications.

vi. Immersing a p-doped silicon substrate (8-12Ω cm) into the above desired 1 mL xanthine-based 1:3:3:3 (verapamil:isoprenaline:superoxide dismutase:adenosine triphosphate) pharmaceutical solutions according to the $L_9$ $(3)^4$ orthogonal design protocol, and storing at −4° C. for 96 hours.

vii. The results of this practice example profiled that the height of quantum wire array is 3.5 nm (FIG. 5); the I-V curve presented a bi-stable electrical property, i.e., the higher current of 1.021 pA and the lower current of −23.998 pA occurred within the ±6V bias potentials (FIG. 14a); the differential conductance spectrum (dI/dV) revealed the quantized kondo effect, i.e., the maximum conductance peak of 67.2825 pA/V located at the −1.917V bias potential (FIG. 14b); the frequency-phase-energy spectrum (FPP) showed phase transitions from 0 degrees to −11512 degrees within the frequency domain from ±50000 Hz to 7.2475E-12 Hz, where 128(−½π) or 64(−π) spin echo or 32(−2π) typical electron spins occurred at the y axis with the central frequency of 7.2475E-12 Hz at the x axis and the energy fluctuation of 0.01581 eV (FIG. 14c); the time-phase-energy spectrum (TPP) presented phase transitions from zero degree to 11512 degrees within the time domain from 0 μs to 1000 μs, where 128(½π) or 64(π) spin echo or 32(2π) typical electron spins happened at the y axis with the central time of 513 μs at the x axis and the energy fluctuation of 0.00395 eV at the z axis (FIG. 14d). The parental data in FIG. 14c-d simultaneously revealed ±(½π) N, ±(π) N and ±(2π) N typical electron spins-driven qubits.

Example 4

Liquid pharmaceutical ingredients were prepared according to the pharmaceutical standards. Reference may be made to pharmaceutical standard guideline issued by the Ministry of Health in China. Topographic structure and qubit features of the 2:1:2:3 molar mixture ratios obtained in Example 4 are depicted in FIGS. 6 and 15a-d.

Figure 15A:
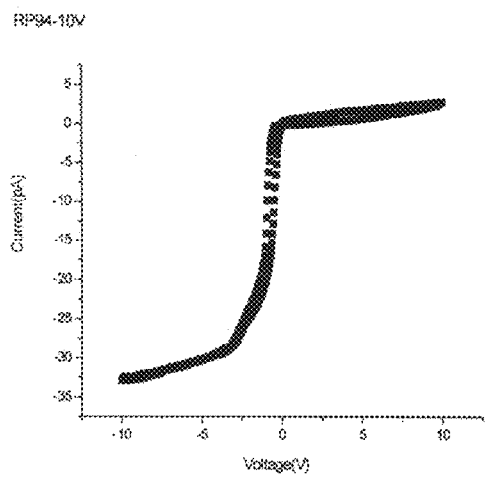
FIG. 15. The PCI (C-AFM) measures the I-V curve of 5 pA~-32.5 pA quantum tunneling hysteresis and 0 pA quantum Hall effect (a, X axis=Voltage, Y axis=Current), the kondo effect conductance spectrum of 40 pA/V~55 pA/V maximum differential conductance peak at 0V and -2V bias potentials (b, X axis=Voltage, Y axis=Conductance), the energy-frequency-phase spectrum (c, X axis=Frequency, Y axis=Phase, Z axis=Energy) and the energy-time-phase spectrum (d, X axis=Time, Y axis=Phase, Z axis=Energy) of ±8V, ±9V and ±10V bias potential-initiated π-½π-π electron spin shuttling for qubits, all of them correspond to FIG. 6.
Figure 15B:
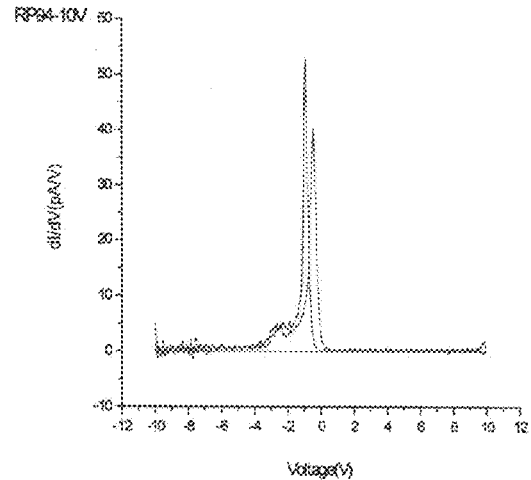
Figure 15C:
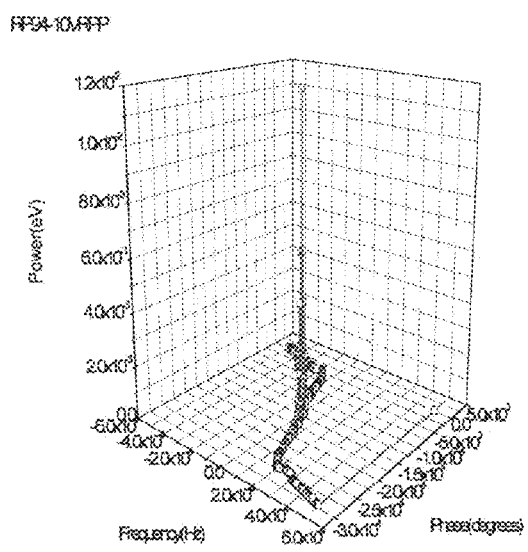
Figure 15D:
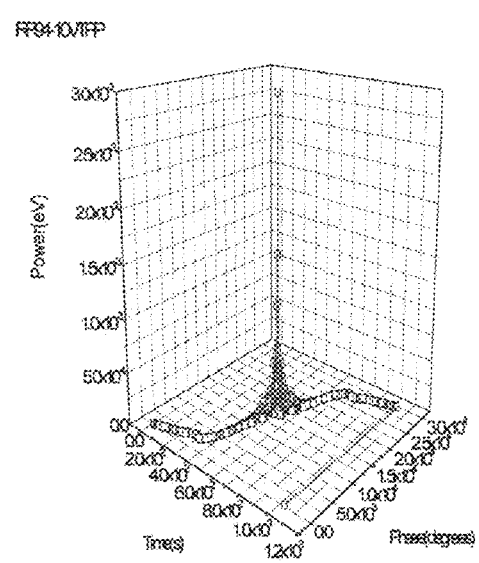

The following pharmaceutical solutions were prepared according to the pharmaceutical standards (see, for example, pharmaceutics guideline of the ministry of health in China):

i. Preparing a verapamil hydrochloride pharmaceutical liquid at a concentration of 2.5 mg/5 mL.

ii. Preparing an isoprenaline hydrochloride pharmaceutical liquid at a concentration of 2 mg/100 mL.

iii. Preparing a physiological buffer solution of superoxide dismutase at a concentration of 1 mg/2 mL.

iv. Preparing a physiological buffer solution of adenosine triphosphate at a concentration of 20 mg/3.3 mL.

v. Respectively preparing and taking the optimum molecular numbers from each ingredients of verapmil in a range of about 20 zeptoMol to about 0.001 zeptoMol, isoprenaline in a range of about 210 zeptoMol to about 0.001 zeptoMol, superoxide dismutase in a range of about 1 zeptoMol to about 0.001 zeptoMol, adenosine triphosphate in a range of 260 zeptoMol to about 1 zeptoMol and xanthine in a range of about 50 μM to about 5 mM, respectively mixing them at room temperature and preparing xanthine-based quaternary pharmaceutical ingredient physiological buffer solutions at molar mixture ratios of 2:1:2:3 (verapamil:isoprenaline:superoxide dismutase:adenosine triphosphate), mixing them at room temperature according to the $L_9 (3)^4$ orthogonal design protocol, keeping xanthine-based quaternary pharmaceutical ingredient physiological buffer solutions in the 1 mL final volume at −4° C. for applications.

vi. Immersing a p-doped silicon substrate (8-12Ω cm) into the above desired 1 mL of xanthine-based 2:1:2:3 (verapamil:isoprenaline:superoxide dismutase:adenosine triphosphate) desired pharmaceutical solutions according to the $L_9 (3)^4$ orthogonal design protocol, and storing at −4° C. for 96 hours.

vii. The results of this practice example profiled that the height of quantum wire array is 6 nm (FIG. 6); the I-V curve presented a bi-stable electrical property, i.e., the higher current of 2.07 pA and the lower current of −32.834 pA occurred within the ±10V bias potentials (FIG. 15a); the differential conductance spectrum (dI/dV) revealed the quantized kondo effect, i.e., the maximum conductance peak of 53.2375 pA/V located at the −0.96V bias potential (FIG. 15b); the frequency-phase-energy spectrum (FPP) showed phase transitions from 180 degrees to −14580 degrees within the frequency domain from ±50000 Hz to 7.2475E-12 Hz, where 126 (−½π) or 81(−π) spin echo typical electron spins occurred at the y axis with the central frequency of 7.2475E-12 Hz at the x axis and the energy fluctuation of 9.58648E-9 eV (FIG. 15c); the time-phase-energy spectrum (TPP) presented phase transitions from 180 degrees to 14940 degrees within the time domain from 0 μs to 1000 μs, where 166(½π) or 63(π) spin echo typical electron spins happened at the y axis with the central time of 513 μs at the x axis and the energy fluctuation of 0.00298 eV at the z axis (FIG. 15d). The parental data in FIG. 15c-d simultaneously revealed ±(½π) N and ±(π) N typical electron spins-driven qubits.

Example 5

Liquid pharmaceutical ingredients were prepared according to the pharmaceutical standards. Reference may be made to pharmaceutical standard guideline issued by the Ministry of Health in China. Topographic structure and qubit features of the 2:2:3:1 molar mixture ratios obtained in Example 5 are depicted in FIGS. 7 and 16a-d.

Figure 16A:
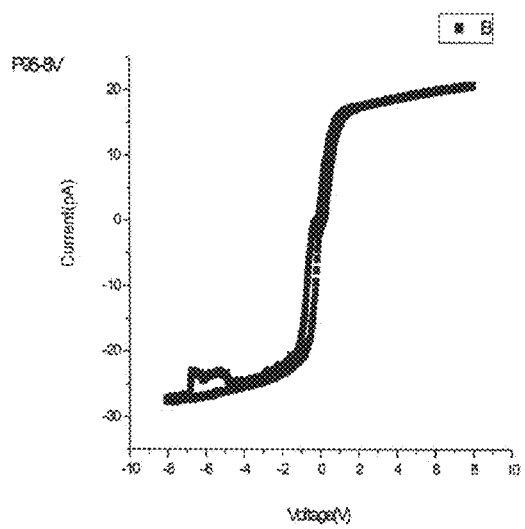
FIG. 16. The PCI (C-AFM) measures the I-V curve of 20 pA~-30 pA quantum tunneling hysteresis and 0 pA quantum Hall effect (a, X axis=Voltage, Y axis=Current), the kondo effect conductance spectrum of 55 pA/V maximum differential conductance peak at 0V bias potential (b, X axis=Voltage, Y axis=Conductance), the energy-frequency-phase spectrum (c, X axis=Frequency, Y axis=Phase, Z axis=Energy) and the energy-time-phase spectrum (d, X axis=Time, Y axis=Phase, Z axis=Energy) of ±7V and ±9V bias potential-initiated zero-½π-2π electron spin shuttling for qubits, all of them correspond to FIG. 7.
Figure 16:
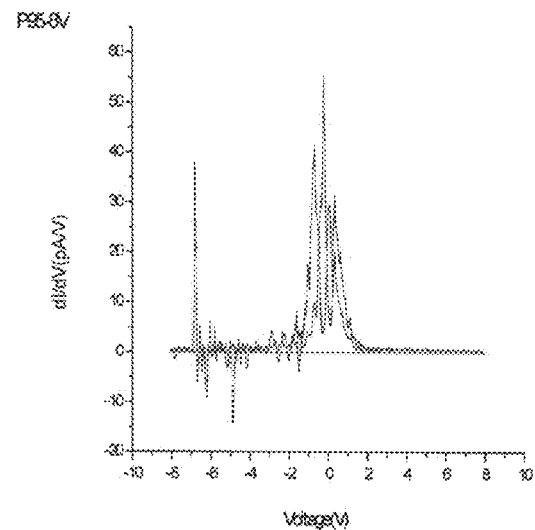
Figure 16:
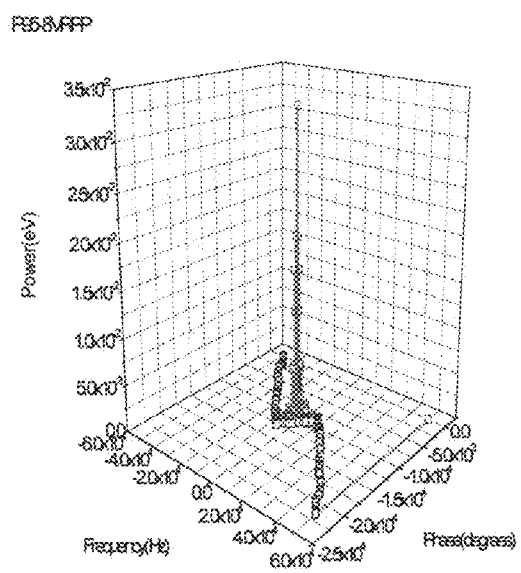
Figure 16:
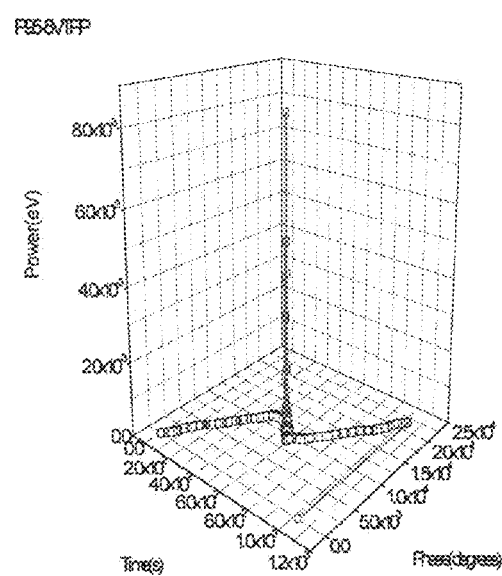

The following pharmaceutical solutions were prepared according to the pharmaceutical standards (see, for example, pharmaceutics guideline of the ministry of health in China):
  i. Preparing aA verapamil hydrochloride pharmaceutical liquid at a concentration of 2.5 mg/5 mL.
  ii. Preparing an isoprenaline hydrochloride pharmaceutical liquid at a concentration of 2 mg/100 mL.
  iii. Preparing aA physiological buffer solution of superoxide dismutase at a concentration of 1 mg/2 mL.
  iv. Preparing aA physiological buffer solution of adenosine triphosphate at a concentration of 20 mg/3.3 mL.
  v. Respectively preparing and taking the optimum molecular numbers from each ingredients of verapmil in a range of about 20 zeptoMol to about 0.001 zeptoMol, isoprenaline in a range of about 210 zeptoMol to about 0.001 zeptoMol, superoxide dismutase in a range of about 1 zeptoMol to about 0.001 zeptoMol, adenosine triphosphate in a range of 260 zeptoMol to about 1 zeptoMol and xanthine in a range of about 50 μM to about 5 mM, respectively mixing them at room temperature and preparing xanthine-based quaternary pharmaceutical ingredient physiological buffer solutions at molar mixture ratios of 2:2:3:1 (verapamil:isoprenaline:superoxide dismutase:adenosine triphosphate), mixing them at room temperature according to the $L_9 (3)^4$ orthogonal design protocol, keeping the 1 mL final volume of xanthine-based quaternary pharmaceutical ingredient physiological buffer solutions −4° C. for applications.

vi. Immersing a p-doped silicon substrate (8-12Ω cm) into the above desired 1 mL 2:2:3:1 (verapamil:isoprenaline:superoxide dismutase:adenosine triphosphate) pharmaceutical ingredient solution according to the $L_9 (3)^4$ orthogonal design protocol, and storing at −4° C. for 96 hours.

vii. The results of this practice example profiled that the height of quantum wire array is 8 nm (FIG. 7); the I-V curve presented a bi-stable electrical property, i.e., the higher current of 20.723 pA and the lower current of −27.549 pA occurred within the ±8V bias potentials (FIG. 16a); the differential conductance spectrum (dI/dV) revealed the quantized kondo effect, i.e., the maximum conductance peak of 55.5468 pA/V located at the −0.223V bias potential (FIG. 16b); the frequency-phase-energy spectrum (FPP) showed phase transitions from 0 degrees to −10800 degrees within the frequency domain from ±50000 Hz to 7.2475E-12 Hz, where 120(−½π) or 40(−1½π) or 240(−¼π) or 60(−π) spin echo typical electron spins occurred at the y axis with the central frequency of 7.2475E-12 Hz at the x axis and the energy fluctuation of 0.0332 eV (FIG. 16c); the time-phase-energy spectrum (TPP) presented phase transitions from 0 degrees to 10800 degrees within the time domain from 0 μs to 1000 μs, where 120(½π) or 40(1½π) or 240(¼π) or 60(π) spin echo typical electron spins happened at the y axis with the central time of 513 μs at the x axis and the energy fluctuation of 0.00833 eV at the z axis (FIG. 16d). The parental data in FIG. 16c-d simultaneously revealed ±(½π) N, ±(1½π) N, ±(¼π) N and ±(π) N typical electron spins-driven qubits.

Example 6

Liquid pharmaceutical ingredients were prepared according to the pharmaceutical standards. Reference may be made to pharmaceutical standard guideline issued by the Ministry of Health in China. Topographic structure and qubit features of the 3:1:3:2 molar mixture ratios obtained in Example 6 are depicted in FIGS. 8 and 17a-d.

Figure 17A:
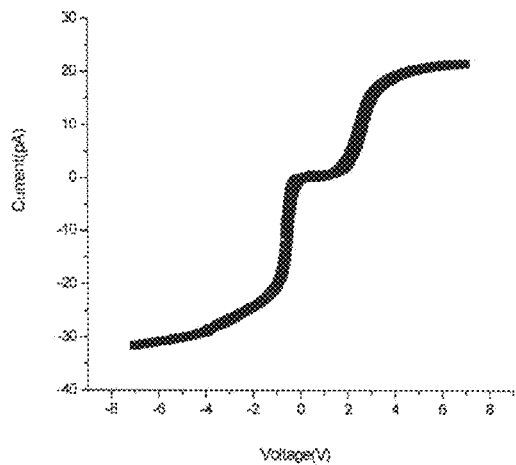
FIG. 17. The PCI (C-AFM) measures the I-V curve of 25 pA~30 pA quantum tunneling hysteresis and 0 pA quantum Hall effect at 0V bias potential (a, X axis=Voltage, Y axis=Current), the kondo effect conductance spectrum of 65 pA/V maximum differential conductance peak at 0V bias potential (b, X axis=Voltage, Y axis=Conductance), the energy-frequency-phase spectrum (c, X axis=Frequency, Y axis=Phase, Z axis=Energy) and the energy-time-phase spectrum (d, X axis=Time, Y axis=Phase, Z axis=Energy) of ±8V, ±9V and ±10V bias potential-initiated zero-½π-π and zero -½π-2π electron spin shuttling for qubits, all of them correspond to FIG. 8.
Figure 17B:
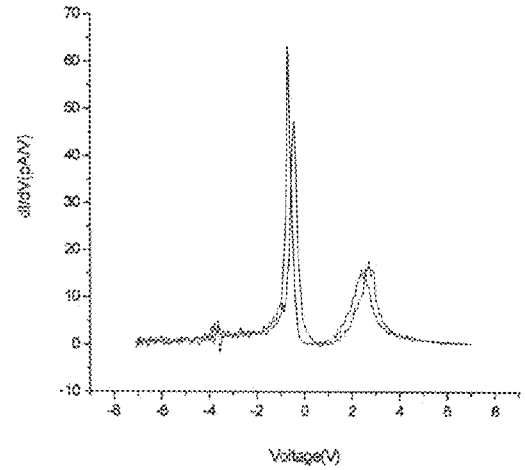
Figure 17C:
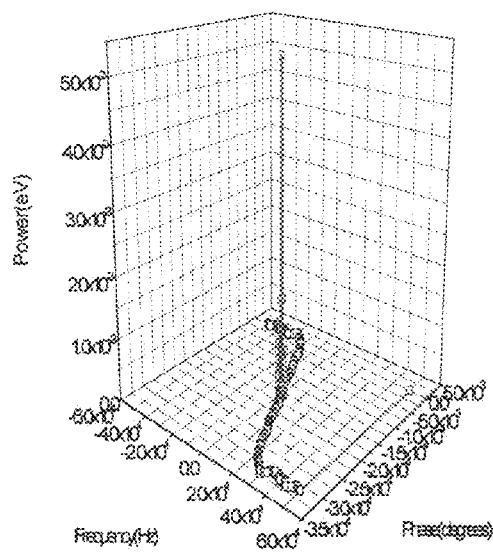
Figure 17D:
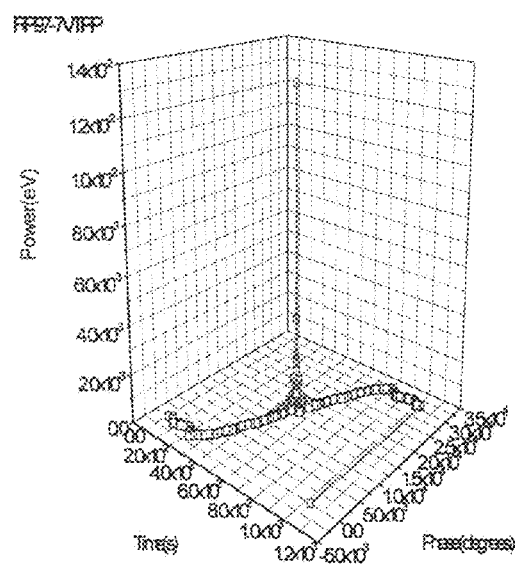

The following pharmaceutical solutions were prepared according to the pharmaceutical standards (see, for example, pharmaceutics guideline of the ministry of health in China):
  i. Preparing a verapamil hydrochloride pharmaceutical liquid at a concentration of 2.5 mg/5 mL.
  ii. Preparing an isoprenaline hydrochloride pharmaceutical liquid at a concentration of 2 mg/100 mL.
  iii. Preparing a physiological buffer solution of superoxide dismutase at a concentration of 1 mg/2 mL.
  iv. Preparing a physiological buffer solution of adenosine triphosphate at a concentration of 20 mg/3.3 mL.
  v. Respectively preparing and taking the optimum molecular numbers from each ingredients of verapmil in a range of about 20 zeptoMol to about 0.001 zeptoMol, isoprenaline in a range of about 210 zeptoMol to about 0.001 zeptoMol, superoxide dismutase in a range of about 1 zeptoMol to about 0.001 zeptoMol, adenosine triphosphate in a range of 260 zeptoMol to about 1 zeptoMol and xanthine in a range of about 50 μM to about 5 mM, respectively mixing them at room temperature and preparing xanthine-based quaternary pharmaceutical ingredient physiological buffer solutions at molar mixture ratios of 3:1:3:2 (verapamil:isoprenaline:superoxide dismutase:adenosine triphosphate), mixing them at room temperature according to the $L_9 (3)^4$ orthogonal design protocol, keeping the 1 mL final volume of xanthine-based quaternary pharmaceutical ingredient physiological buffer solutions at −4° C. for applications.

vi. Immersing a p-doped silicon substrate (8-12Ω cm) into the above desired 1 mL 3:1:3:2 (verapamil:isoprenaline: superoxide dismutase:adenosine triphosphate) xanthine-based quaternary pharmaceutical ingredient physiological buffer solutions according to the $L_9 (3)^4$ orthogonal design protocol, and storing at −4° C. for 96 hours.

vii. The results of this practice example profiled that the height of quantum wire array is 4.5 nm (FIG. 8); the I-V curve presented a bi-stable electrical property, i.e., the higher current of 21.576 pA and the lower current of −31.509 pA occurred within the ±7V bias potentials (FIG. 17a); the differential conductance spectrum (dI/dV) reveals the quantized kondo effect, i.e., the maximum conductance peak of 63.5786 pA/V located at the −0.715V bias potential (FIG. 17b); the frequency-phase-energy spectrum (FPP) showed phase transitions from 0 degrees to −15480 degrees within the frequency domain from ±50000 Hz to 7.2475E-12 Hz, where 172(½π) or 81(−π) spin echo typical electron spins occurred at the y axis with the central frequency of 7.2475E-12 Hz at the x axis and the energy fluctuation of 0.05289 eV (FIG. 17c); the time-phase-energy spectrum (TPP) presented phase transitions from 0 degrees to 10800 degrees within the time domain from 0 μs to 1000 μs, where 172(½π) or 81(π) spin echo typical electron spins happened at the y axis with the central time of 513 μs at the x axis and the energy fluctuation of 0.01322 eV at the z axis (FIG. 17d). The parental data in FIG. 17c-d simultaneously revealed ±(½π) N and ±(π) N typical electron spins-driven qubits.

Example 7

Liquid pharmaceutical ingredients were prepared according to the pharmaceutical standards. Reference may be made to pharmaceutical standard guideline issued by the Ministry of Health in China. Topographic structure and qubit features of the 3:2:1:3 molar mixture ratios obtained in Example 7 are depicted in FIGS. 9 and 18a-d.

Figure 18A:
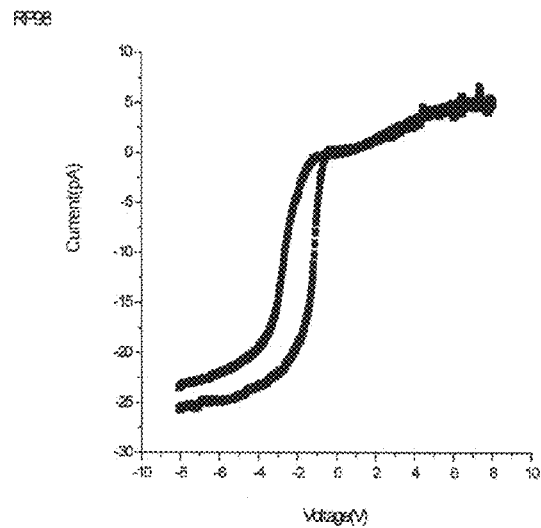
FIG. 18. The PCI (C-AFM) measures the I-V curve of 5 pA~-25 pA quantum tunneling hysteresis (a, X axis=Voltage, Y axis=Current), the kondo effect conductance spectrum of 35 pA/V maximum differential conductance peak at -1V bias potential (b, X axis=Voltage, Y axis=Conductance), the energy-frequency-phase spectrum (c, X axis=Frequency, Y axis=Phase, Z axis=Energy) and the energy-time-phase spectrum (d, X axis=Time, Y axis=Phase, Z axis=Energy) of ±8V, ±9V and ±10V bias potential-initiated N zero-½π-2π and N π-½π-2π electron spin shuttling for qubits, all of them correspond to FIG. 9.
Figure 18B:
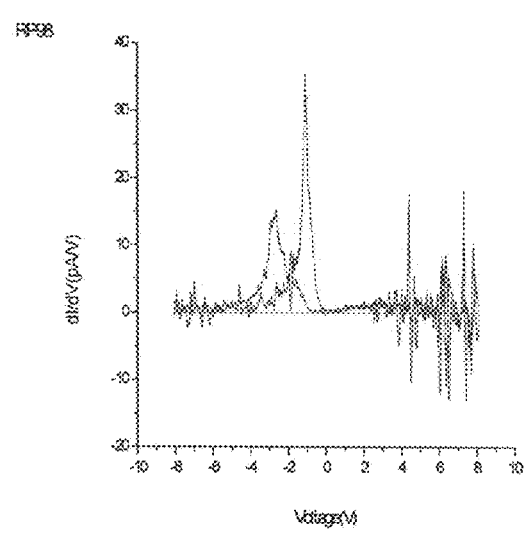
Figure 18C:
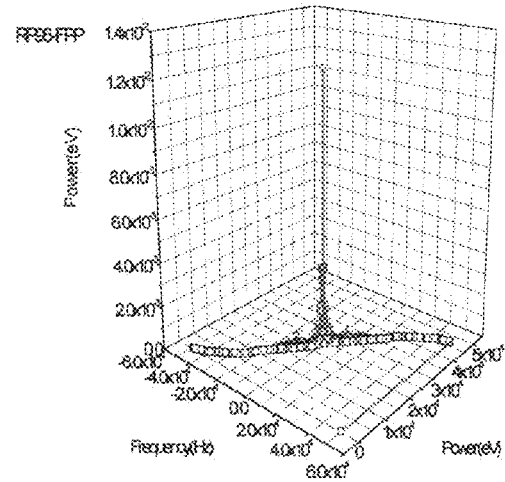
Figure 18D:
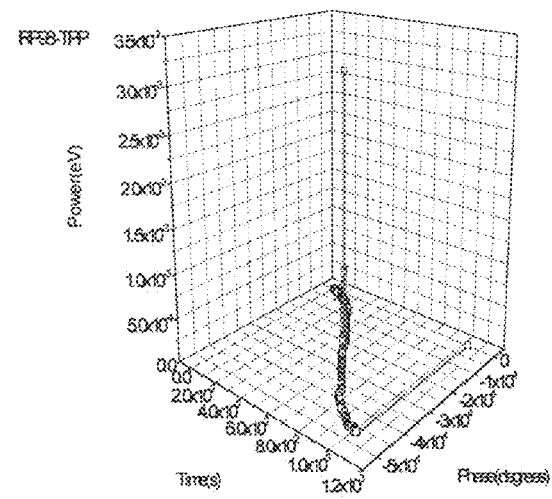

The following pharmaceutical solutions were prepared according to the pharmaceutical standards (see, for example, pharmaceutics guideline of the ministry of health in China):

i. Preparing a verapamil hydrochloride pharmaceutical liquid at a concentration of 2.5 mg/5 mL.

ii. Preparing an isoprenaline hydrochloride pharmaceutical liquid at a concentration of 2 mg/100 mL.

iii. Preparing a physiological buffer solution of superoxide dismutase at a concentration of 1 mg/2 mL.

iv. Preparing a physiological buffer solution of adenosine triphosphate at a concentration of 20 mg/3.3 mL.

v. Respectively preparing and taking the optimum molecular numbers from each ingredients of verapmil in a range of about 20 zeptoMol to about 0.001 zeptoMol, isoprenaline in a range of about 210 zeptoMol to about 0.001 zeptoMol, superoxide dismutase in a range of about 1 zeptoMol to about 0.001 zeptoMol, adenosine triphosphate in a range of 260 zeptoMol to about 1 zeptoMol and xanthine in a range of about 50 μM to about 5 mM, respectively mixing them at room temperature and preparing xanthine-based quaternary pharmaceutical ingre-dient physiological buffer solutions at molar mixture ratios of 3:2:1:3 (verapamil:isoprenaline:superoxide dismutase:adenosine triphosphate), mixing them at room temperature according to the $L_9 (3)^4$ orthogonal design protocol, keeping the 1 mL final volume of xanthine-based quaternary pharmaceutical ingredient physiological buffer solutions at −4° C. for applications.

vi. Immersing a p-doped silicon substrate (8-12Ω cm) into the above desired 1 mL 3:2:1:3 (verapamil:isoprenaline: superoxide dismutase:adenosine triphosphate) pharmaceutical ingredient solution according to the $L_9 (3)^4$ orthogonal design protocol, and storing at −4° C. for 96 hours.

vii. The results of this practice example profiled that the height of quantum wire array is 50 nm (FIG. 9); the I-V curve presented a bi-stable electrical property, i.e., the higher current of 5.478 pA and the lower current of −25.614 pA occurred within the ±8V bias potentials (FIG. 18a); the differential conductance spectrum (dI/dV) revealed the quantized kondo effect, i.e., the maximum conductance peak of 35.5468 pA/V located at the −1.096V bias potential (FIG. 18b); the frequency-phase-energy spectrum (FPP) showed phase transitions from 180 degrees to 23580 degrees within the frequency domain from ±50000 Hz to 7.2475E-12 Hz, where 262 (½π) or 32(2π) or 64(π) spin echo typical electron spins occurred at the y axis with the central frequency of 7.2475E-12 Hz at the x axis and the energy fluctuation of 0.01244 eV (FIG. 18c); the time-phase-energy spectrum (TPP) presented phase transitions from 0 degrees to −23220 degrees within the time domain from 0 μs to 1000 μs, where 158(−½π) or 69(−2π) or 78(−π) spin echo typical electron spins happened at the y axis with the central time of 513 μs at the x axis and the energy fluctuation of 0.00311 eV at the z axis (FIG. 18d). The parental data in FIG. 18c-d simultaneously revealed ±(½π) N, ±(π) N and ±(2π) N typical electron spins-driven qubits.

Example 8

Liquid pharmaceutical ingredients were prepared according to the pharmaceutical standards (reference may be made to pharmaceutical standard guideline issued by the Ministry of Health in China). Topographic structure and qubit features of the 1:2:2:1 molar mixture ratios obtained in Example 8 are depicted in FIGS. 1 and 10a-d.

The following pharmaceutical solutions were prepared according to the pharmaceutical standards (see for example, pharmaceutics guideline of the ministry of health in China):

i. Preparing a verapamil hydrochloride pharmaceutical liquid at a concentration of 2.5 mg/5 mL.

ii. Preparing an isoprenaline hydrochloride pharmaceutical liquid at a concentration of 2 mg/100 mL.

iii. Preparing a physiological buffer solution of superoxide dismutase at a concentration of 1 mg/2 mL.

iv. Preparing a physiological buffer solution of adenosine triphosphate at a concentration of 20 mg/3.3 mL.

v. Respectively preparing and taking the optimum molecular numbers from each ingredients of verapmil in a range of about 20 zeptoMol to about 0.001 zeptoMol, isoprenaline in a range of about 210 zeptoMol to about 0.001 zeptoMol, superoxide dismutase in a range of about 1 zeptoMol to about 0.001 zeptoMol, adenosine triphosphate in a range of 260 zeptoMol to about 1 zeptoMol and xanthine in a range of about 50 μM to about 5 mM, respectively mixing them at room temperature and preparing xanthine-based quaternary pharmaceutical ingredient physiological buffer solutions at molar mixture ratios of 1:2:2:1 (verapamil:isoprenaline:superoxide dismutase:adenosine triphosphate), mixing them at room temperature according to the $L_9$ $(3)^4$ orthogonal design protocol, keeping the 1 mL final volume of xanthine-based quaternary pharmaceutical ingredient physiological buffer solutions at $-4°$ C. for applications.

vi. Immersing a p-doped silicon substrate (8-12Ω cm) into the above desired 1 mL 1:2:2:1 (verapamil:isoprenaline: superoxide dismutase:adenosine triphosphate) pharmaceutical ingredient solutions according to the $L_9$ $(3)^4$ orthogonal design protocol, and storing at $-4°$ C. for 96 hours.

vii. The results of this practice example profiled that the height of quantum wire array is 3 nm (FIG. 1); the I-V curve presented a bi-stable electrical property, i.e., the higher current and the lower current of ±34.581 pA occur within the ±9V bias potentials (FIG. 10a); the differential conductance spectrum (dI/dV) revealed the quantized kondo effect, i.e., the maximum conductance peak of 140.51389 pA/V located at the $-3.25$V bias potential (FIG. 10b); the frequency-phase-energy spectrum (FPP) showed phase transitions from 0 degrees to $-19080$ degrees within the frequency domain of ±50000 Hz~7.2475E-12 Hz, where 254($-½π$) or 127($-π$) spin echo typical electron spins occurred at the y axis with the central frequency of 7.2475E-12 Hz at the x axis and the energy fluctuation of 0.05027 eV (FIG. 10c); the time-phase-energy spectrum (TPP) presented phase transitions from 0 degrees to 19080 degrees within the time domain from 0 μs to 1000 μs, where 254(½π) or 127(π) spin echo typical electron spins happened at the y axis with the central time of 513 μs at the x axis and the energy fluctuation of 0.0124 eV at the z axis (FIG. 10d). The parental data in FIG. 10c-d simultaneously revealed ±(½π) N typical electron spins-driven qubits.

Example 9

Liquid pharmaceutical ingredients were prepared according to the pharmaceutical standards (see for example, pharmaceutical standard guideline issued by the Ministry of Health in China). Topographic structure and qubit features of the 2:2:1:2 molar mixture ratios obtained in Example 9 are depicted in FIGS. 1 and 11a-d.

The following pharmaceutical solutions were prepared according to the pharmaceutical standards (see, for example, pharmaceutics guideline of the ministry of health in China):

i. Preparing a verapamil hydrochloride pharmaceutical liquid at a concentration of 2.5 mg/5 mL.

ii. Preparing an isoprenaline hydrochloride pharmaceutical liquid at a concentration of 2 mg/100 mL.

iii. Preparing a physiological buffer solution of superoxide dismutase at a concentration of 1 mg/2 mL.

iv. Preparing a physiological buffer solution of adenosine triphosphate at a concentration of 20 mg/3.3 mL.

v. Respectively preparing and taking the optimum molecular numbers from each ingredients of verapmil in a range of about 20 zeptoMol to about 0.001 zeptoMol, isoprenaline in a range of about 210 zeptoMol to about 0.001 zeptoMol, superoxide dismutase in a range of about 1 zeptoMol to about 0.001 zeptoMol, adenosine triphosphate in a range of about 260 zeptoMol to about 1 zeptoMol and xanthine in a range of about 50 μM to about 5 mM, respectively mixing them at room temperature and preparing xanthine-based quaternary pharmaceutical ingredient physiological buffer solutions at molar mixture ratios of 2:2:1:2 (verapamil:isoprenaline:superoxide dismutase:adenosine triphosphate), mixing them at room temperature according to the $L_9$ $(3)^4$ orthogonal design protocol, keeping the 1 mL final volume of xanthine-based quaternary pharmaceutical ingredient solutions at $-4°$ C. for applications.

vi. Immersing a p-doped silicon substrate (8-12Ω cm) into the above desired 1 mL 2:2:1:2 (verapamil:isoprenaline: superoxide dismutase:adenosine triphosphate) pharmaceutical ingredient solutions according to the $L_9$ $(3)^4$ orthogonal design protocol, and storing at $-4°$ C. for 96 hours.

vii. The results of this practice example profiled that the height of quantum wire array is 16 nm (FIG. 2); the I-V curve presented a bi-stable electrical property, i.e., the higher current of 3.568 pA and the lower current of $-22.19$ pA occurred within the ±2V bias potentials (FIG. 11a); the differential conductance spectrum (dI/dV) revealed the quantized kondo effect, i.e., the maximum conductance peak of 315.62 pA/V located at the $-0.874$V bias potential (FIG. 11b); the frequency-phase-energy spectrum (FPP) showed phase transitions from 0 degrees to 18540 degrees within the ±50000 Hz-7.2475E-12 Hz frequency domain, where 206(½π) or 103(π) spin echo typical electron spins occurred at the y axis with the central frequency of 7.2475E-12 Hz at the x axis and the energy fluctuation of 0.14939 eV (FIG. 11c); the time-phase-energy spectrum (TPP) presented phase transitions from 0 degrees to $-181800$ degrees within the 0 μs to 1000 μs time domain, where 202(±½π) or 101($-π$) spin echo typical electron spins happened at the y axis with the central time of 513 μs at the x axis and the energy fluctuation of 0.01116 eV at the z axis (FIG. 11d). The parental data in FIG. 11c-d simultaneously revealed ±(½π) N and ±(π) N typical electron spins-driven qubits.

What is claimed is:

1. A bi-stable quantum wire array of self-assembled nanomedicine molecules, comprising:
   a silicon substrate; and
   a self-assembled vertical structure of a quinary complex including verapamil, isoprenaline, superoxide dismutase, adenosine triphosphate, and xanthine formed on the silicon substrate,
   wherein the self-assembled vertical structure has a bi-stable electrical hysteresis with qubits in current-voltage (I-V) curves being in a range of $-35$ pA to $+35$ pA quantum tunneling hysteresis, and an energy-time-phase spectrum in a range of $-10$ V to $+10$ V.

2. The bi-stable quantum wire array according to claim 1, wherein the self-assembled vertical structure has a cigar-shape.

3. The bi-stable quantum wire array according to claim 1, wherein the silicon substrate includes a p-doped surface or an n-doped surface.

4. The bi-stable quantum wire array according to claim 1, wherein qubits in current-voltage (I-V) curves are in a range of $-32.834$ pA to $+21.576$ pA quantum tunneling hysteresis.

5. A method for preparing the bi-stable quantum wire array as in claim 1, the method comprising:
   preparing a hydrochloride verapamil solution;
   preparing a hydrochloride isoprenaline solution;
   preparing a superoxide dismutase in physiological buffer solution;
   preparing an adenosine triphosphate in physiological buffer solution;

preparing a xanthine in physiological buffer solution;
preparing a mixture solution by mixing the hydrochloride verapamil solution, the hydrochloride isoprenaline solution, the superoxide dismutase in physiological buffer solution, the adenosine triphosphate in physiological buffer solution and the xanthine in physiological buffer solution;
providing the mixture solution onto a surface of the silicon substrate; and
providing a condition for self-assembly of verapamil, isoprenaline, superoxide dismutase, adenosine triphosphate, and xanthine for forming the self-assembled vertical structure of the quinary complex on the surface of the silicon substrate.

6. The method according to claim 5, wherein the providing the condition includes cooling the mixture solution on the surface at −4° C.

7. The method according to claim 6, wherein a duration of the cooling the mixture solution on the surface is for 96 hours.

8. The method according to claim 5, wherein the providing the condition includes cooling the mixture solution on the surface for 96 hours.

\* \* \* \* \*